(12) United States Patent
Modzelewski et al.

(10) Patent No.: US 6,562,625 B2
(45) Date of Patent: May 13, 2003

(54) DISTINGUISHING TEST TYPES THROUGH SPECTRAL ANALYSIS

(75) Inventors: Brent E. Modzelewski, Brookfield, CT (US); Steven B. Gilmour, Coral Gables, FL (US)

(73) Assignee: Home Diagnostics, Inc., Fort Lauderdale, FL (US)

(*) Notice: Subject to any disclaimer, the term of this patent is extended or adjusted under 35 U.S.C. 154(b) by 52 days.

(21) Appl. No.: 09/794,044

(22) Filed: Feb. 28, 2001

(65) Prior Publication Data

US 2002/0160517 A1 Oct. 31, 2002

(51) Int. Cl.⁷ .............................................. G01N 21/78
(52) U.S. Cl. .......................... 436/44; 436/63; 436/67; 436/164; 422/82.05; 422/82.09
(58) Field of Search .................. 422/82.05, 82.08, 422/82.09; 436/63, 67, 164, 165, 169, 170, 172; 356/448

(56) References Cited

U.S. PATENT DOCUMENTS

| | | |
|---|---|---|
| 2,297,248 A | 9/1942 | Rudolph |
| 2,369,499 A | 2/1945 | Treuhaft |
| 2,893,843 A | 7/1959 | Adams |
| 2,893,844 A | 7/1959 | Cook |
| 3,061,523 A | 10/1962 | Free |
| 3,092,465 A | 6/1963 | Adams |
| 3,099,605 A | 7/1963 | Free |
| 3,127,281 A | 3/1964 | Meyer |
| 3,232,710 A | 2/1966 | Rieckmann |
| 3,298,789 A | 1/1967 | Mast |
| 3,413,198 A | 11/1968 | Deutsch |
| 3,443,903 A | 5/1969 | Haack |
| 3,483,031 A | 12/1969 | Lauer |
| 3,501,009 A | 3/1970 | Jaworek |
| 3,506,126 A | 4/1970 | Serfass |

(List continued on next page.)

FOREIGN PATENT DOCUMENTS

| | | |
|---|---|---|
| AU | 45033/85 | 1/1986 |
| AU | 76758/87 | 2/1988 |
| CA | 1117784 | 2/1982 |
| CA | 1219797 | 3/1987 |
| DE | 34 39 181 | 10/1984 |
| DE | 39 21 391 | 1/1991 |
| EP | 0 095 057 | 11/1983 |

(List continued on next page.)

OTHER PUBLICATIONS

The Merck Index, tenth edition (1983), p. 199.*
Adler, S. et al., "Automatic Coagulation Profile System," Advances in Automated Analysis, Technicon International Congress 1970, vol. I, pp. 421–424 (1971).
Adlercreutz, H. et al., "Evaluation of the New System Olli 3000 Kinetic Ultraviolet Analyzer for Measuring Aspartate and Alanine Aminotransferase and Lactate Dehydrogenase Activities in Serum," Clinical Chemistry, vol. 21, No. 6, p. 676–84 (1975).

(List continued on next page.)

*Primary Examiner*—Jeffrey Snay
(74) *Attorney, Agent, or Firm*—McDonnell Boehnen Hulbert & Berghoff

(57) ABSTRACT

A method and apparatus for automatically selecting test types for an analytical meter system based on the insertion into the meter of a test element. The test element can be an analytical element, formed by a test strip with a fluid such as blood applied thereto; a control element, formed by a test strip with control fluid applied thereto; or a standard element, or a standard strip exhibiting known optical properties. By inserting the test element into the analytical meter system, optical properties are measured and the existence of relationships between the measurements are ascertained. Based on the existence or nonexistence of certain relationships, the proper test can be automatically selected by the meter without the need for user interaction. Advantageously, the results of the test can be classified and stored according to test type.

27 Claims, 6 Drawing Sheets

U.S. PATENT DOCUMENTS

| | | |
|---|---|---|
| 3,509,025 A | 4/1970 | Bergmeyer |
| 3,511,608 A | 5/1970 | Anderson |
| 3,552,925 A | 1/1971 | Fetter |
| 3,552,928 A | 1/1971 | Fetter |
| 3,560,161 A | 2/1971 | Webb |
| 3,577,162 A | 5/1971 | Gaehwiler |
| 3,591,480 A | 7/1971 | Neff |
| 3,593,568 A | 7/1971 | Schmitz |
| 3,604,815 A | 9/1971 | Clemens |
| 3,607,093 A | 9/1971 | Stone |
| 3,620,677 A | 11/1971 | Morison |
| 3,630,957 A | 12/1971 | Rey |
| 3,650,698 A | 3/1972 | Adler |
| 3,653,836 A | 4/1972 | Gruber |
| 3,658,480 A | 4/1972 | Kane |
| 3,660,638 A | 5/1972 | Oberli |
| 3,663,175 A | 5/1972 | Depositar |
| 3,672,838 A | 6/1972 | Trcka |
| 3,677,901 A | 7/1972 | Bergmeyer |
| 3,690,833 A | 9/1972 | Ferrari |
| 3,703,336 A | 11/1972 | Rosse |
| 3,709,612 A | 1/1973 | Clemens |
| 3,713,986 A | 1/1973 | Bergmeyer |
| 3,715,192 A | 2/1973 | Wenz |
| 3,718,439 A | 2/1973 | Rosse |
| 3,723,064 A | 3/1973 | Liotta |
| 3,748,044 A | 7/1973 | Liston |
| 3,762,609 A | 10/1973 | Hagen |
| 3,765,841 A | 10/1973 | Paulson |
| 3,769,178 A | 10/1973 | Rothermel |
| 3,775,058 A | 11/1973 | Bush |
| 3,775,595 A | 11/1973 | Rosse |
| 3,778,350 A | 12/1973 | Bergmeyer |
| 3,785,772 A | 1/1974 | Coggeshall |
| 3,791,933 A | 2/1974 | Moyer |
| 3,795,149 A | 3/1974 | Gillette |
| 3,795,484 A | 3/1974 | Daly |
| 3,798,004 A | 3/1974 | Zerachia |
| 3,802,843 A | 4/1974 | Kim |
| 3,804,593 A | 4/1974 | Smythe |
| 3,811,840 A | 5/1974 | Bauer |
| 3,814,582 A | 6/1974 | Rohrbaugh |
| 3,819,863 A | 6/1974 | Slaght |
| 3,822,285 A | 7/1974 | Werner |
| 3,837,339 A | 9/1974 | Aisenberg et al. |
| 3,847,553 A | 11/1974 | Verbeck |
| 3,853,472 A | 12/1974 | Rittersdorf |
| 3,864,166 A | 2/1975 | Barker |
| 3,876,374 A | 4/1975 | Burns |
| 3,881,992 A | 5/1975 | Ralston |
| 3,897,214 A | 7/1975 | Lange |
| 3,901,657 A | 8/1975 | Lightfoot |
| 3,902,052 A | 8/1975 | Amar |
| 3,907,503 A | 9/1975 | Betts |
| 3,910,701 A | 10/1975 | Henderson |
| 3,915,647 A | 10/1975 | Wright |
| 3,917,452 A | 11/1975 | Rittersdorf |
| 3,917,453 A | 11/1975 | Milligan |
| 3,919,051 A | 11/1975 | Koch |
| 3,926,736 A | 12/1975 | Bucolo |
| 3,929,581 A | 12/1975 | de Fonseca-Wollheim |
| 3,933,593 A | 1/1976 | Sternberg |
| 3,936,357 A | 2/1976 | Milligan |
| 3,942,995 A | 3/1976 | Ichikawa |
| 3,950,133 A | 4/1976 | Monte |
| 3,954,342 A | 5/1976 | Boeke |
| 3,957,436 A | 5/1976 | Murray |
| 3,958,560 A | 5/1976 | March. |
| 3,960,497 A | 6/1976 | Acord |
| 3,964,870 A | 6/1976 | Tiedemann |
| 3,971,630 A | 7/1976 | Sandrock |
| 3,973,129 A | 8/1976 | Blumberg |
| 3,973,189 A | 8/1976 | Angel |
| 3,975,398 A | 8/1976 | Werner |
| 3,979,274 A | 9/1976 | Newman |
| 3,980,437 A | 9/1976 | Kishimoto |
| 3,983,005 A | 9/1976 | Goodhue |
| 3,985,508 A | 10/1976 | Williams |
| 3,986,833 A | 10/1976 | Mast |
| 3,988,208 A | 10/1976 | Werner |
| 3,990,849 A | 11/1976 | Lee |
| 3,992,158 A | 11/1976 | Przybylowicz |
| 4,009,615 A | 3/1977 | Ruhl |
| 4,011,046 A | 3/1977 | Labes |
| 4,014,321 A | 3/1977 | March |
| 4,015,121 A | 3/1977 | Gagnon |
| 4,022,577 A | 5/1977 | Brooker |
| 4,038,485 A | 7/1977 | Johnston |
| 4,040,786 A | 8/1977 | Trivedi |
| 4,042,335 A | 8/1977 | Clement |
| 4,043,756 A | 8/1977 | Sommervold |
| 4,050,898 A | 9/1977 | Goffe |
| 4,056,468 A | 11/1977 | Breiter |
| 4,057,394 A | 11/1977 | Genshaw |
| 4,059,405 A | 11/1977 | Sodickson |
| 4,061,468 A | 12/1977 | Lange |
| 4,061,469 A | 12/1977 | DuBose |
| 4,066,362 A | 1/1978 | Carter |
| 4,066,403 A | 1/1978 | Bruschi |
| 4,068,169 A | 1/1978 | Angel |
| 4,069,017 A | 1/1978 | Wu |
| 4,076,502 A | 2/1978 | Dugle |
| 4,095,272 A | 6/1978 | Janzen |
| 4,098,574 A | 7/1978 | Dappen |
| 4,101,276 A | 7/1978 | Anderson |
| 4,109,159 A | 8/1978 | Onillon |
| 4,110,079 A | 8/1978 | Schaeffer |
| 4,125,327 A | 11/1978 | Margolis |
| 4,125,372 A | 11/1978 | Kawai |
| 4,128,628 A | 12/1978 | Brooker |
| 4,135,883 A | 1/1979 | McNeil |
| 4,144,306 A | 3/1979 | Figueras |
| 4,152,390 A | 5/1979 | Nosco |
| 4,153,668 A | 5/1979 | Hill |
| 4,160,646 A | 7/1979 | Furutani |
| 4,165,508 A | 8/1979 | Barter |
| 4,176,008 A | 11/1979 | Figueras |
| 4,178,153 A | 12/1979 | Sodickson |
| 4,180,060 A | 12/1979 | Kutter |
| 4,199,260 A | 4/1980 | Kusnetz |
| 4,199,261 A | 4/1980 | Tidd |
| 4,211,845 A | 7/1980 | Genshaw |
| 4,217,107 A | 8/1980 | Saito |
| 4,218,144 A | 8/1980 | Whitehouse et al. |
| 4,219,529 A | 8/1980 | Tersteeg |
| 4,224,032 A | 9/1980 | Glover |
| 4,226,537 A | 10/1980 | Colley |
| 4,230,456 A | 10/1980 | Wu |
| 4,233,029 A | 11/1980 | Columbus |
| 4,238,196 A | 12/1980 | Acuff |
| 4,240,912 A | 12/1980 | Stumpf |
| 4,253,846 A | 3/1981 | Smythe |
| 4,254,083 A | 3/1981 | Columbus |
| 4,255,384 A | 3/1981 | Kitajima |
| 4,255,788 A | 3/1981 | Schwartz |
| 4,256,693 A | 3/1981 | Kondo |
| 4,257,862 A | 3/1981 | Schnipelsky |
| 4,258,001 A | 3/1981 | Pierce |
| 4,261,041 A | 4/1981 | Starr |
| 4,269,938 A | 5/1981 | Frank |
| 4,272,482 A | 6/1981 | Jessop |

| | | | | | |
|---|---|---|---|---|---|
| 4,273,868 A | 6/1981 | Walter | 4,503,385 A | 3/1985 | Haynes |
| 4,274,832 A | 6/1981 | Wu | 4,503,555 A | 3/1985 | Brimhall, Jr. |
| 4,276,051 A | 6/1981 | Ginsberg | 4,509,859 A | 4/1985 | Markart |
| 4,277,561 A | 7/1981 | Monget | 4,517,160 A | 5/1985 | Galle |
| 4,278,439 A | 7/1981 | White | 4,518,259 A | 5/1985 | Ward |
| 4,281,062 A | 7/1981 | Kallis | 4,523,853 A | 6/1985 | Rosenbladt et al. |
| 4,283,383 A | 8/1981 | Masson | 4,528,159 A | 7/1985 | Liston |
| 4,283,491 A | 8/1981 | Dappen | 4,532,107 A | 7/1985 | Siddigi |
| 4,288,228 A | 9/1981 | Oberhardt | 4,534,012 A | 8/1985 | Yokozawa |
| 4,292,272 A | 9/1981 | Kitajima | 4,540,670 A | 9/1985 | Arai |
| 4,297,238 A | 10/1981 | Vormbrock | 4,547,460 A | 10/1985 | Eikenberry |
| 4,298,345 A | 11/1981 | Sodickson | 4,551,307 A | 11/1985 | Koyama |
| 4,298,688 A | 11/1981 | Kallies | 4,552,458 A | 11/1985 | Lowne |
| 4,299,916 A | 11/1981 | Litman | 4,553,848 A | 11/1985 | Rosicke |
| 4,300,906 A | 11/1981 | Negersmith | 4,554,132 A | 11/1985 | Collins |
| 4,302,420 A | 11/1981 | Jakubowicz | 4,557,901 A | 12/1985 | Koyama |
| 4,303,406 A | 12/1981 | Ross | 4,562,148 A | 12/1985 | Sommer |
| 4,303,408 A | 12/1981 | Kim | 4,567,024 A | 1/1986 | Koyama |
| 4,303,753 A | 12/1981 | Lam | 4,576,793 A | 3/1986 | Koyama |
| 4,308,485 A | 12/1981 | Ignazio | 4,578,245 A | 3/1986 | Arai |
| 4,310,399 A | 1/1982 | Columbus | 4,578,248 A | 3/1986 | Nagaoka |
| 4,312,834 A | 1/1982 | Vogel | 4,587,100 A | 5/1986 | Amano |
| 4,318,984 A | 3/1982 | Magers | 4,587,220 A | 5/1986 | Mayambala-Mwanika |
| 4,318,985 A | 3/1982 | Bauer | 4,592,365 A | 6/1986 | Georgi |
| 4,325,910 A | 4/1982 | Jordan | 4,592,893 A | 6/1986 | Poppe |
| 4,330,299 A | 5/1982 | Cerami | 4,594,224 A | 6/1986 | Okaniwa |
| 4,336,330 A | 6/1982 | Bauer | 4,594,327 A | 6/1986 | Zuk |
| 4,337,065 A | 6/1982 | Hiratsuka | 4,595,562 A | 6/1986 | Liston |
| 4,338,279 A | 7/1982 | Orimo | 4,602,995 A | 7/1986 | Cassaday |
| 4,340,669 A | 7/1982 | Bauer | 4,603,428 A | 7/1986 | Sandrik |
| 4,353,983 A | 10/1982 | Siddiqi | 4,604,254 A | 8/1986 | Yamamoto |
| 4,353,984 A | 10/1982 | Yamada | 4,604,264 A | 8/1986 | Rothe |
| 4,361,648 A | 11/1982 | Shuenn-tzong | 4,604,579 A | 8/1986 | Cannon |
| 4,363,874 A | 12/1982 | Greenquist | 4,618,475 A | 10/1986 | Wang |
| 4,366,061 A | 12/1982 | Papanek et al. | 4,622,207 A | 11/1986 | Wang |
| 4,366,241 A | 12/1982 | Tom | 4,627,014 A | 12/1986 | Lo |
| 4,370,983 A | 2/1983 | Lichtenstein | 4,627,445 A | 12/1986 | Garcia |
| 4,373,818 A | 2/1983 | Yamamoto | 4,632,559 A | 12/1986 | Brunsting |
| 4,384,042 A | 5/1983 | Milke | 4,637,403 A | 1/1987 | Garcia |
| 4,390,343 A | 6/1983 | Walter | 4,637,978 A | 1/1987 | Dappen |
| 4,390,621 A | 6/1983 | Bauer | 4,642,286 A | 2/1987 | Moldowan |
| 4,391,905 A | 7/1983 | Bauer | 4,647,430 A | 3/1987 | Zweig |
| 4,391,906 A | 7/1983 | Bauer | 4,647,432 A | 3/1987 | Wakatake |
| 4,399,099 A | 8/1983 | Buckles | 4,649,123 A | 3/1987 | Charlton |
| 4,403,984 A | 9/1983 | Ash | 4,661,319 A | 4/1987 | Lape |
| 4,407,959 A | 10/1983 | Tsuji | 4,668,619 A | 5/1987 | Greenquist |
| 4,415,700 A | 11/1983 | Betz | 4,669,878 A | 6/1987 | Meier |
| 4,418,037 A | 11/1983 | Katsuyama | 4,670,218 A | 6/1987 | Gantzer |
| 4,420,564 A | 12/1983 | Tsuji | 4,671,937 A | 6/1987 | Katsuyama |
| 4,420,566 A | 12/1983 | Jessop | 4,676,653 A | 6/1987 | Strohmeier et al. |
| 4,427,632 A | 1/1984 | Okaniwa | 4,685,059 A | 8/1987 | Yamamoto |
| 4,427,889 A | 1/1984 | Muller | 4,686,479 A | 8/1987 | Young |
| 4,430,299 A | 2/1984 | Horne | 4,687,329 A | 8/1987 | Schultz |
| 4,430,427 A | 2/1984 | Hopkins | 4,693,985 A | 9/1987 | Degen |
| 4,430,436 A | 2/1984 | Koyama | 4,703,756 A | 11/1987 | Gough et al. |
| 4,448,207 A | 5/1984 | Parrish | 4,710,458 A | 12/1987 | Maines |
| 4,450,153 A | 5/1984 | Hopkins | 4,714,341 A | 12/1987 | Hamaguri |
| 4,452,887 A | 6/1984 | Kitajima | 4,717,546 A | 1/1988 | Barnett |
| 4,458,539 A | 7/1984 | Bilstad | 4,731,726 A | 3/1988 | Allen |
| 4,459,358 A | 7/1984 | Berke | 4,732,736 A | 3/1988 | Kobayashi |
| 4,460,684 A | 7/1984 | Bauer | 4,734,360 A | 3/1988 | Phillips |
| 4,464,172 A | 8/1984 | Lichtenstein | 4,748,114 A | 5/1988 | Kallies |
| 4,472,498 A | 9/1984 | Masuda | 4,772,561 A | 9/1988 | Genshaw |
| 4,472,505 A | 9/1984 | Manabe | 4,773,097 A | 9/1988 | Suzaki |
| 4,476,222 A | 10/1984 | Ohtani | 4,774,192 A | 9/1988 | Terminiello |
| 4,477,575 A | 10/1984 | Vogel | 4,775,637 A | 10/1988 | Sutherland |
| 4,478,942 A | 10/1984 | Katsuyama | 4,780,283 A | 10/1988 | Meinecke |
| 4,478,944 A | 10/1984 | Gross | 4,782,511 A | 11/1988 | Nemec et al. |
| 4,483,924 A | 11/1984 | Tsuji | 4,787,398 A | 11/1988 | Garcia |
| 4,492,462 A | 1/1985 | Pross | 4,790,979 A | 12/1988 | Terminiello |
| 4,499,052 A | 2/1985 | Fulwyler | 4,791,461 A | 12/1988 | Kishimoto |

| Patent | Date | Name |
|---|---|---|
| 4,803,153 A | 2/1989 | Shibata |
| 4,803,159 A | 2/1989 | Smith-Lewis |
| 4,803,625 A | 2/1989 | Fu |
| 4,810,470 A | 3/1989 | Burkhardt |
| 4,814,142 A | 3/1989 | Gleisner |
| 4,816,224 A | 3/1989 | Vogel |
| 4,818,710 A | 4/1989 | Sutherland |
| 4,820,489 A | 4/1989 | Rothe |
| 4,820,649 A | 4/1989 | Kawaguchi |
| 4,824,639 A | 4/1989 | Hildenbrand |
| 4,839,297 A | 6/1989 | Freitag |
| 4,849,340 A | 7/1989 | Oberhardt |
| 4,855,108 A | 8/1989 | Masuda |
| 4,857,273 A | 8/1989 | Stewart |
| 4,866,836 A | 9/1989 | Von Brandt et al. |
| 4,870,005 A | 9/1989 | Akiyoshi |
| 4,876,204 A | 10/1989 | Inoue |
| 4,876,207 A | 10/1989 | Mack |
| 4,877,747 A | 10/1989 | Stewart |
| 4,889,131 A | 12/1989 | Salem et al. |
| 4,889,815 A | 12/1989 | Bradwell |
| 4,900,666 A | 2/1990 | Phillips |
| 4,909,260 A | 3/1990 | Salem et al. |
| 4,935,346 A | 6/1990 | Phillips et al. |
| 4,970,172 A | 11/1990 | Kundu |
| 4,974,607 A | 12/1990 | Miwa |
| 4,981,779 A | 1/1991 | Wagner |
| 4,985,205 A | 1/1991 | Fritsche et al. |
| 4,994,238 A | 2/1991 | Daffern et al. |
| 5,019,574 A | 5/1991 | Miura et al. |
| 5,029,583 A | 7/1991 | Meserol et al. |
| 5,036,852 A | 8/1991 | Leishman |
| 5,039,225 A | 8/1991 | Uekusa |
| 5,049,487 A | 9/1991 | Phillips et al. |
| 5,059,394 A | 10/1991 | Phillips et al. |
| 5,071,769 A | 12/1991 | Kundu |
| 5,079,715 A | 1/1992 | Venkataraman et al. |
| 5,114,350 A | 5/1992 | Hewett |
| 5,179,005 A | 1/1993 | Phillips et al. |
| 5,187,100 A | 2/1993 | Matzinger et al. |
| 5,188,968 A | 2/1993 | Kano et al. |
| 5,207,263 A | 5/1993 | Maier et al. |
| 5,225,997 A | 7/1993 | Lederer et al. |
| 5,231,576 A | 7/1993 | Suzuki et al. |
| 5,246,858 A | 9/1993 | Arbuckle et al. |
| 5,251,126 A | 10/1993 | Kahn et al. |
| 5,279,294 A | 1/1994 | Anderson et al. |
| 5,281,395 A | 1/1994 | Markart et al. |
| 5,296,192 A | 3/1994 | Carroll et al. |
| 5,302,348 A | 4/1994 | Cusack et al. |
| 5,304,468 A | 4/1994 | Phillips et al. |
| 5,316,727 A | 5/1994 | Suzuki et al. |
| 5,321,492 A | 6/1994 | Detwiler et al. |
| 5,321,618 A | 6/1994 | Gessman |
| 5,339,821 A | 8/1994 | Fujimoto |
| 5,367,555 A | 11/1994 | Isoyama |
| 5,371,020 A | 12/1994 | Frischauf |
| 5,379,214 A | 1/1995 | Arbuckle et al. |
| 5,390,238 A | 2/1995 | Kirk et al. |
| 5,408,535 A * | 4/1995 | Howard et al. ............. 356/421 |
| 5,416,695 A | 5/1995 | Stutman et al. |
| 5,418,142 A | 5/1995 | Kiser et al. |
| 5,424,035 A | 6/1995 | Hönes et al. |
| 5,424,545 A | 6/1995 | Block et al. |
| 5,431,880 A | 7/1995 | Kramer |
| 5,452,343 A | 9/1995 | Garland et al. |
| 5,453,360 A | 9/1995 | Yu |
| 5,462,051 A | 10/1995 | Oka et al. |
| 5,467,475 A | 11/1995 | Takahashi et al. |
| 5,470,752 A | 11/1995 | Burd et al. |
| 5,515,170 A | 5/1996 | Matzinger et al. |
| 5,518,689 A | 5/1996 | Dosmann et al. |
| 5,520,883 A | 5/1996 | Charlton et al. |
| 5,526,120 A | 6/1996 | Jina et al. |
| 5,529,755 A | 6/1996 | Higashio et al. |
| 5,545,877 A | 8/1996 | Shelton |
| 5,548,633 A | 8/1996 | Kujawa et al. |
| 5,563,042 A | 10/1996 | Phillips et al. |
| 5,573,506 A | 11/1996 | Vasko |
| 5,576,952 A | 11/1996 | Stutman et al. |
| 5,579,001 A | 11/1996 | Dempsey et al. |
| 5,579,775 A | 12/1996 | Dempsey et al. |
| 5,581,369 A | 12/1996 | Righter et al. |
| 5,597,532 A | 1/1997 | Connolly |
| 5,605,150 A | 2/1997 | Radons et al. |
| 5,605,837 A | 2/1997 | Karimi et al. |
| 5,620,863 A | 4/1997 | Tomasco et al. |
| 5,622,429 A | 4/1997 | Heinze |
| 5,639,672 A | 6/1997 | Burd et al. |
| 5,666,404 A | 9/1997 | Ciccotelli et al. |
| 5,681,529 A | 10/1997 | Taguchi et al. |
| 5,695,949 A | 12/1997 | Galen et al. |
| 5,704,364 A | 1/1998 | Saltzstein et al. |
| 5,704,366 A | 1/1998 | Tacklind et al. |
| 5,715,823 A | 2/1998 | Wood et al. |
| 5,719,034 A | 2/1998 | Kiser et al. |
| 5,725,774 A | 3/1998 | Neyer |
| 5,728,352 A | 3/1998 | Poto et al. |
| 5,735,285 A | 4/1998 | Albert et al. |
| 5,745,308 A | 4/1998 | Spangenberg |
| 5,753,452 A | 5/1998 | Smith |
| 5,754,111 A | 5/1998 | Garcia |
| 5,755,942 A | 5/1998 | Zanzucchi et al. |
| 5,762,871 A | 6/1998 | Neyer |
| 5,764,158 A | 6/1998 | Franklin et al. |
| 5,770,389 A | 6/1998 | Ching et al. |
| 5,770,839 A | 6/1998 | Ruebush et al. |
| 5,772,586 A | 6/1998 | Heinonen et al. |
| 5,772,963 A | 6/1998 | Cantatore et al. |
| 5,780,304 A | 7/1998 | Matzinger et al. |
| 5,782,878 A | 7/1998 | Morgan et al. |
| 5,785,650 A | 7/1998 | Akasaka et al. |
| 5,789,664 A * | 8/1998 | Neel et al. .................... 356/39 |
| 5,791,342 A | 8/1998 | Woodard |
| 5,827,180 A | 10/1998 | Goodman |
| 5,837,546 A | 11/1998 | Allen et al. |
| 5,840,020 A | 11/1998 | Heinonen et al. |
| 5,841,846 A | 11/1998 | Abbruscato |
| 5,842,975 A | 12/1998 | Illyés et al. |
| 5,843,692 A | 12/1998 | Phillips et al. |
| 5,846,486 A | 12/1998 | Pugh |
| 5,850,320 A | 12/1998 | Warmka et al. |
| 5,866,349 A | 2/1999 | Lilja et al. |
| 5,872,627 A | 2/1999 | Miers |
| 5,885,839 A | 3/1999 | Lingane et al. |
| 5,922,530 A | 7/1999 | Yu |
| 5,945,341 A * | 8/1999 | Howard, III ................. 422/58 |
| 5,962,215 A | 10/1999 | Douglas et al. |
| 5,986,754 A | 11/1999 | Harding |
| 5,989,917 A | 11/1999 | McAleer et al. |
| 5,995,236 A | 11/1999 | Roth et al. |
| 5,997,817 A | 12/1999 | Crismore et al. |
| 6,027,692 A | 2/2000 | Galen et al. |
| 6,032,352 A | 3/2000 | Furay et al. |
| 6,040,195 A | 3/2000 | Carroll et al. |
| 6,067,463 A | 5/2000 | Jeng et al. |
| 6,084,660 A | 7/2000 | Shartle |
| 6,168,957 B1 | 1/2001 | Matzinger et al. |
| 6,193,873 B1 | 2/2001 | Ohara et al. |
| 6,201,607 B1 | 3/2001 | Roth et al. |
| 6,226,082 B1 | 5/2001 | Roe |
| 6,233,471 B1 | 5/2001 | Berner et al. |

FOREIGN PATENT DOCUMENTS

| | | |
|---|---|---|
| EP | 0 110 173 | 6/1984 |
| EP | 0 112 166 | 6/1984 |
| EP | 0 113 896 | 7/1984 |
| EP | 0 133 481 | 2/1985 |
| EP | 0 140 337 | 5/1985 |
| EP | 0 141 648 | 5/1985 |
| EP | 0 159 727 | 10/1985 |
| EP | 0 166 878 | 1/1986 |
| EP | 0 169 055 | 1/1986 |
| EP | 0 173 500 | 3/1986 |
| EP | 0 182 647 | 5/1986 |
| EP | 0 183 524 | 6/1986 |
| EP | 0 225 561 A3 | 12/1987 |
| EP | 0 256 806 | 2/1988 |
| EP | 0 271 854 | 6/1988 |
| EP | 0 295 526 | 12/1988 |
| EP | 0 336 483 | 10/1989 |
| EP | 0 345 781 | 12/1989 |
| EP | 0 407 800 | 6/1990 |
| EP | 0 414 563 | 2/1991 |
| EP | 0 415 679 | 3/1991 |
| EP | 0 473 241 | 3/1992 |
| EP | 0 475 692 | 3/1992 |
| EP | 0 479 394 | 4/1992 |
| EP | 0 511 120 | 10/1992 |
| EP | 0 555 045 | 8/1993 |
| EP | 0 574 134 | 12/1993 |
| EP | 0 735 369 | 3/1995 |
| EP | 0 656 423 | 7/1995 |
| EP | 0 759 555 | 8/1995 |
| EP | 0 769 558 | 10/1995 |
| EP | 0 779 367 | 12/1995 |
| EP | 0 800 082 | 4/1996 |
| EP | 0 764 271 | 3/1997 |
| EP | 0 779 984 | 6/1997 |
| EP | 0 781 405 | 7/1997 |
| EP | 0 781 406 | 7/1997 |
| EP | 0 799 896 | 10/1997 |
| EP | 0 816 849 | 1/1998 |
| EP | 0 823 634 | 2/1998 |
| EP | 0 823 635 | 2/1998 |
| EP | 0 823 636 | 2/1998 |
| EP | 0 826 777 | 3/1998 |
| EP | 0 832 691 | 4/1998 |
| EP | 0 852 336 | 7/1998 |
| EP | 0 960 946 | 12/1999 |
| EP | 0 974 840 | 1/2000 |
| FR | 2191734 | 2/1974 |
| GB | 835551 | 5/1960 |
| GB | 911181 | 11/1962 |
| GB | 1037155 | 7/1966 |
| GB | 1485506 | 9/1977 |
| GB | 2029012 | 3/1980 |
| GB | 2026160 | 6/1980 |
| GB | 2039035 | 7/1980 |
| GB | 2090659 | 7/1982 |
| JP | 54-113383 | 9/1979 |
| JP | 55-136957 | 10/1980 |
| JP | 55-155235 | 12/1980 |
| JP | 56-057937 | 5/1981 |
| JP | 56-164941 | 12/1981 |
| JP | 56-168148 | 12/1981 |
| JP | 57-101760 | 6/1982 |
| JP | 57-163848 | 10/1982 |
| JP | 57-168144 | 10/1982 |
| JP | 58-021544 | 2/1983 |
| JP | 59-032850 | 2/1984 |
| JP | 59-032851 | 2/1984 |
| JP | 59-108942 | 6/1984 |
| JP | 59-182347 | 10/1984 |
| JP | 61-026842 | 2/1986 |
| JP | 61-068539 | 4/1986 |
| JP | 61-155849 | 7/1986 |
| JP | 61-292540 | 12/1986 |
| JP | 62-22066 | 1/1987 |
| JP | 62-298765 | 12/1987 |
| JP | 63-021558 | 1/1988 |
| JP | 63-175749 | 7/1988 |
| JP | 1-119743 | 1/1989 |
| JP | 7-311196 | 7/1995 |
| JP | 8-75735 | 3/1996 |
| SU | 172088 | 12/1965 |
| WO | 81/00622 | 3/1981 |
| WO | 81/00912 | 4/1981 |
| WO | 83/00931 | 3/1983 |
| WO | 84/02578 | 7/1984 |
| WO | 92/12428 | 7/1992 |
| WO | 92/15861 | 9/1992 |
| WO | 94/02578 | 2/1994 |
| WO | 96/07757 | 3/1996 |
| WO | 96/07892 | 3/1996 |
| WO | 96/07893 | 3/1996 |
| WO | 96/07907 | 3/1996 |
| WO | 96/07908 | 3/1996 |
| WO | 97/46878 | 12/1997 |
| WO | 99/46591 | 9/1999 |

OTHER PUBLICATIONS

Al–Kaissi, E. et al., "Assessment of Substrates for Horseradish Peroxidase in Enzyme Immunoassay," Journal of Immunological Methods, 58, pp. 127–132 (1983).

Article (ECRI): "Blood Glucose Monitors," Health Devices, vol. 17, No. 9, pp. 253–271 (Sep. 1988).

Bandi, Z.L. et al., "Extended Clinical Trial and Evaluation of Glucose Determination with the Eastman Kodak Ektachem GLU/BUN Analyzer," Clinical Chemistry, vol. 27, No. 1, pp. 27–34 (1981).

Bell, P.M. et al., "Benefits of Self Monitoring of Blood Glucose," British Medical Journal, vol. 286, pp. 1230–1231, Apr. 16, 1983.

Billmeyer, F.W. Jr., et al., Principles of Color Technology, Second Edition, John Wiley & Sons, Inc. 1981.

Bio–Dynamics Corp.,"Coagulation Unimeter CU500 Series Technical Service Manual," Nov., 1982.

Capaldi, Dante J. et al., "A New Peroxidase Color Reaction: Oxidative Coupling of 3–Methyl–2–Benzothiazolinone Hydrazone (MBTH) with its Formaldehyde Azine Application to Glucose and Choline Oxidases," Analytical Biochemistry, 129, 329–336 (1983).

Carrick, C.E., "Barriers to Performance of Maintenance and Quality Control (QC) by Patients Using Home Glucose Meters," Diabetes, May 1990, vol. 39, Supp. 1, The Program for the 50th Annual Meeting of the American Diabetes Association in Atlanta, Georgia, Abstract #205.

Cate, J.C. IV, "Evaluation of an Engineering Model of the 'Ektachem' Analyzer for Glucose and Urea Assay," Clinical Chemistry, vol. 26, No. 2, p. 266 (1980).

Chance, B., "Rapid and Sensitive Spectrophotometry. III. A Double Beam Apparatus," Rev. Sci. Instru., 22, pp. 634–638 (1951).

Chua, K.S., et al., "Plasma Glucose Measurement with the Yellow Springs Glucose Analyzer," Clinical Chemistry, vol. 24, No. 1, pp. 150–152 (1978).

Cohen, M. et al., "Home Blood–Glucose Monitoring—A New approach to the Management of Diabetes Mellitus," Med. J. Aust. 1980; 2: 713–716.

Cohen, Matthew et al., "Self–Monitoring of Blood Glucose Levels in Non–Insulin–Dependent Diabetes Mellitus," Med. J. Aust. 1983; 2: 377–380.

Cowles, J.C., "Theory of Dual–Wavelength Spectrophotometry for Turbid Samples," Journal of the Optical Society of America, vol. 55, No. 6, pp. 690–693, Jun. 1965.

Curme, H.G., et al., "Multilayer Film Elements for Clinical Analysis: General Concepts," Clinical Chemistry, vol. 24, No. 8, pp. 1335–1342 (1978).

Damon Corporation, "Instrument Operating Parameters—Damon Microfluorometer," (no date available).

Davidson, J.A., et al., "Evaluation of a New Blood Glucose Meter and Test Strip Intended for Hospital Bedside Glucose Testing," Diabetes, May 1990, vol. 39, Supp. 1, The Program for the 50th Annual Meeting of the American Diabetes Association in Atlanta, Georgia, Abstract #871.

De Pasqua, A., et al., "Errors in Blood Glucose Determination," The Lancet, p. 1165 (1984).

Driscoll, R.C., et al., "Discrete Automated Chemistry System with Tableted Reagents," Clinical Chemistry, vol. 29, No. 9, pp. 1609–1615 (1983).

Eastman Kodak Co., "DT60 Analyzer Operator's Manual," Pub. No. C–50, Part No. 632071, Jul. 1986.

Eastman Kodak Co., "Kodak Ektachem DT Slides: (GLU)—Glucose Test Methodology," Pub. No. C–300, Copyright 1986.

Eastman Kodak Co., "Kodak Ektachem DT Slides—Test Methodology—Glucose," Pub. No. C–300 (1992).

Eastman Kodak Co., "Normal Operation for the Kodak Ektachem DTSC Module," Pub. No. XP3100–5, Sep. 1991.

Elliott, R. J., "Ektachem DT60 Analyzer," Physicians & Computers vol. 2, No. 6, pp. 13–16 (Oct. 1984).

European Patent Office Opposition File, European Patent 0 256 806, granted on Application No. 873–7014.8, Lifescan, Inc., Opposition by Boehringer Mannheim GmbH.

Evenson, M.A., et al., "Peak Characteristics and Computers in Continuous Flow Analysis," Clinical Chemistry, vol. 16, No. 7, pp. 606–611 (1970).

Fairclough et al., "An Evaluation Of Patient Performance Of and Their Satisfaction With Various Rapid Blood Glucose Measurement Systems," Diabetes Care, vol. 6, No. 1, pp. 45–49 (1981).

Feldman, J.M. et al., "Inhibition of Glucose Oxidase Paper Tests by Reducing Metabolites," Diabetes, vol. 19, No. 5, pp. 337–343 (May, 1970).

Finley, P.R. et al., "Evaluation of a New Multichannel Analyzer," Clinical Chemistry, vol. 24, No. 12, p. 2126 (1978).

Fleming, D.R., "Who Benefits from Automatic Record Keeping," Diabetes, May 1990, vol. 39, Supp. 1, The Program for the 50th Annual Meeting of the American Diabetes Asoociation in Atlanta, Georgia, Abstract #862.

Funnell, M.M., et al., "Perceived Effectiveness, Cost and Availability of Patient Education Methods and Materials," Diabetes, May 1990, vol. 39, Supp. 1, The Program for the 50th Annual Meeting of the American Diabetes Association in Atlanta, Georgia, Abstract #200.

Geoghegan, W.D. in "Enzyme–Mediated Immunoassay," Ngo and Lenhoff, ed., pp. 451–465 (1985).

Geoghegan, W.D. et al., "Adaptation of the Ngo–Lenhoff Peroxidase Assay for Solid Phase ELISA," Journal of Immunological Methods, 60, pp. 61–68 (1983).

Gilden, J.L., et al., "Matchmaker: A Visual Reader Improves Monitoring Accuracy, Quality of Life and Glycemic Control in Elderly Diabetics," Diabetes, May 1990, vol. 39, Supp. 1, The Program for the 50th Annual Meeting of the American Diabetes Association in Atlanta, Georgia, Abstract #868.

Hahn B., et al., "Polychromatic Analysis: New Applications of an Old Technique," Clinical Chemistry, vol. 25, No. 6, pp. 951–959 (1979).

Hardin, E., et al., "Clinical Laboratory Evaluation of the Perkin–Elmer KA–150 Enzyme Analyzer," Clinical Chemistry, vol. 22, No. 4, pp. 434–438 (1976).

Havlin, C.E., et al., "Critical Evaluation of Blood Glucose Monitoring Devices," Diabetes, May 1990, vol. 39, Supp. 1, The Program for the 50th Annual Meeting of the American Diabetes Association in Atlanta, Georgia, Abstract #873.

"Healthcare Product Comparison System (HCPS): Blood Glucose Monitors," ECRI, 35 pp. (1999).

Ikeda, Y. et al., "Pilot Study of Self–Measurement of Blood Glucose Using the Dextrostix–Eyetone System for Juvenile–Onset Diabetes," Diabetologia, 15, pp. 91–93 (1978).

Jarrett, L., et al., "Home Blood Glucose Meters with Memories," Diabetes, May 1990, vol. 39, Supp. 1, The Program for the 50th Annual Meeting of the American Diabetes Association in Atlanta, Georgia, Abstract #685.

Keilin, D., "Properties of Glucose Oxidase (Notatin)," Biochem., 42, pp. 221–229 (1948).

Kineiko, R.W., et al., "Laboratory Evaluation of the Boehringer Mannheim 'Hitachi 705' Automatic Analyzer," Clinical Chemistry, vol. 29, No. 4, p. 688 (1983).

Lee, E.Y., et al., "Do Physicians Appropriately Utilize Inpatient Bedside Glucose Monitoring?," Diabetes, May 1990, vol. 39, Supp. 1, The Program for the 50th Annual Meeting of the American Diabetes Association in Atlanta, Georgia, Abstract #883.

Leroux et al., "Ward Level Evaluation Of The 'One Touch' Glucose Meter," Clin. Chem., vol. 34 No. 9, 1988, p. 1928.

Lo, D.H. et al, "Quantitative Estimate of Total Bilirubin in Serum Using the *Kodak Ektachem*Clinical Chemistry Slide," Clinical Chemistry, vol. 30, No. 6, p. 970 (1984).

Lo, D.H. et al., "Quantitative Estimate of Total Bilirubin in Serum Using the Kodak Ektachem Clinical Chemistry Slide (TBIL)," Jul. 31, 1984, (Copyright 1984 Eastman–Kodak).

Medical Laboratory Automation Inc., "Pipette Care and Procedure Manual," (Copyright 1983).

Miles Laboratories, "Seralyzer Operation Manual," (Revised 1/84) including Test Module Inserts (Various revision dates) and Dilution System Instructions (Various revision dates).

Miles Laboratories, "Seralyzer Reflectance Photometer Assay Procedures in Brief" (Revised 8/84).

Morgenstern, Stan et al., "STAC Rate Reaction and Fixed–Point Methods," pp. 16–22, Dec. 1976.

Morris, D.L. et al., "A Chemistry for the Immobilization of Enzymes on Nylon," Biochem. J., vol. 147(3), pp. 593–603 (1975).

Murkin, S.A., et al., "Anchored Instruction (AI) Enhances Diabetes (DM) Problem Solving," Diabetes, May 1990, vol. 39, Supp. 1, The Program for the 50th Annual Meeting of the American Diabetes Association in Atlanta, Georgia, Abstract #65.

Neeley, E. et al., "An Instrument for Digital Matrix Photometry," in Nipper, H. (ed), "Selected Papers on Cliniical Chemistry Instrumentation", AACC Press, Washington, pp. 35–38 (1985).

Neeley, E. et al., "Reflectance Digital Matrix Photometry," in Nipper, H. (ed), "Selected Papers on Clinical Chemistry Instrumentation", AACC Press, Washington, pp. 39–42 (1985).

Neeley, W., et al., "Design and Operation of a Signal Comparator to Increase Efficiency of Continuous–Flow Analyzers," in Nipper, H. (ed), "Selected Papers on Cliniical Chemistry Instrumentation", AACC Press, Washington, pp. 150–152 (1985).

Neeley, W., et al., "Design and Performance of a Miniaturized High–Speed Continuous–Flow Analyzer," in Nipper, H. (ed), "Selected Papers on Cliniical Chemistry Instrumentation", AACC Press, Washington, pp. 153–156 (1985).

Neeley, W., et al., "'High–Performance' Colorimeter with an Electronic Bubble Gate for Use in Miniaturized Continuous–Flow Analyzers," in Nipper, H. (ed), "Selected Papers on Cliniical Chemistry Instrumentation", AACC Press, Washington, pp. 157–161 (1985).

Neely, W. et al., "Multilayer Film Analysis for Glucose in 1–microliter Samples of Plasma," Clinical Chemistry 29/12, pp. 2103–2105 (1985).

Ngo, T.T., et al., "A Sensitive and Versatile Chromogenic Assay for Peroxidase and Peroxidase–Coupled Reactions," Analytical Biochemistry, 105, pp. 389–397 (1980).

Ohkubo et al., "Plasma Glucose Concentrations Of Whole Blood, As Determined With A Multilayer–Film Analytical Element," Clinical Chemistry, vol. 27, No. 7, (1981) pp. 1287–1290.

Passey, R. et al., "Measurement of Spectral Bandwidth, as exemplified with the 'Beckman Enzyme Analyzer System TR' Spectrophotometer," Clinical Chemistry, vol. 21, No. 11, pp. 1582–1584 (1975).

Passey, R., et al., "Evaluation of the Beckman 'System TR Enzyme Analyzer'," Clinical Chemistry, vol. 21, No. 8, pp. 1107–1112 (1975).

Passey, R., et al., "Measurement of Spectral Bandwidth as Exemplified with the Beckman 'Enzyme Analyzer System TR Spectrophotometer'," in Nipper, H. (ed), "Selected Papers on Cliniical Chemistry Instrumentation", AACC Press, Washington, pp. 39–42 (1985).

Pellegrino, L.S., et al., "Pilot study: Blood Glucose Monitors," Diabetes, May 1990, vol. 39, Supp. 1, The Program for the 50th Annual Meeting of the American diabetes Association in Atlanta, Georgia, Abstract #882.

Percy–Robb, I.W., et al., "The Peak Monitor of the Technicon SMAC System," Clinical Chemistry, vol. 24, No. 1, pp. 146–148 (1978).

Polesello A. et al., "Application of Near Infra Red Spectrophotometry to the Nondestructive Analysis of Foods: A Review of Experimental Results," CRC Critical Reviews In Food Science and Nutrition 18(3); 203–30 (1983).

Rachlin, J.A., et al., "User Errors in Blood Glucose Monitoring," Diabetes, May 1990, vol. 39, Supp. 1, The Program for the 50th Annual Meeting of the American Diabetes Association in Atlanta, Georgia, Abstract #879.

Ratzlaff, K.L. et al., "Theoretical Assessment of Precision in Dual Wavelength Spectrophotometric Measurement," Analytical Chemistry, vol. 49, No. 14, pp. 2170–2176, Dec. 1977.

Richards, F.M. et al., "Glutaraldehyde as a Protein Cross–linking Reagent," J. Mol. Biol., 37, pp. 231–233 (1968).

Rikmenspoel, Robert, "The Sensitivity and Accuracy of Dual–Wavelength Spectrophotometers," Applied Optics, vol. 3, No. 3, pp. 351–355, Mar. 1964.

Schocken, D.M., et al., "Marketing Diabetes Education Reaches Primary Care Physicians," Diabetes, May 1990, vol. 39, Supp. 1, The Program for the 50th Annual Meeting of the American Diabetes Association in Atlanta, Georgia, Abstract #66.

Scott, W.E., "Filler Research Studies Improve Papermaking Applications," American Papermaker, pp. 12–14, May 1987.

Shibata, Shozo et al., "Dual–Wavelength Spectrophotometry—Part 1. General Method," Analytica Chimica Acta, 46, pp. 271–279 (1969).

Shirey, T.L., "Development of a Layered–Coating Technology for Clinical Chemistry," Clinical Biochemistry, vol. 16, No. 2, pp. 147–155, 1983.

Shoucri, R,M., et al., "Some Observations on the Kinetics of the Jaffe Reaction for Creatinine," Clinical Chemistry, vol. 23, No. 9, pp. 1527–1530 (1977).

Smith, J., et al., "An Innovative Technology for 'Random–Access' Sampling," in Nipper, H. (ed), "Selected Papers on Cliniical Chemistry Instrumentation", AACC Press, Washington, pp. 193–197 (1985).

Sodickson, L., Presentation Slides (1976–1977).

Soloniewicz, R. et al., "Spectrophotometric Determination of Reducing Sugars with Aromatic Nitro Compounds," Institute of General Chemistry, Technical University, Lodz, Poland, pp. 105–114 (1980).

Songer, T.J., "Health Insurance Characteristics in Families with IDDM Children," Diabetes, May 1990, vol. 39, Supp. 1, The Program for the 50th Annual Meeting of the American Diabetes Association in Atlanta, Georgia, Abstract #210.

Sönksen, P.H. et al., "Home Monitoring of Blood–Glucose—Method for Improving Diabetic Control," The Lancet, vol. 1978:1, No. 8067, pp. 729–732 (Apr. 8, 1978).

Spayd, R.W., et al., "Multilayer Film Elements for Clinical Analysis: Applications to Representative Chemical Determinations," Clinical Chemistry, vol. 24, No. 8, pp. 1343–1350 (1978).

Sternberg, J.C. et al., "Spectrophotometric Analysis of Multicomponent Systems Using the Least Squares Method in Matrix Form: The Ergosterol Irradiation System," Analytical Chemistry, vol. 32, No. 1, Jan. 1960, pp. 84–90.

Sundaram et al., "Routine Glucose Determination In Serum By Use Of An Immobilized Glucose Dehydrogenase Nylon–Tube Reactor," Clinical Chemistry, vol. 25, No. 8, (1979) pp. 1436–1439.

Table: "Effects of Sample Volume and Anticoagulant on Ektachem Accuracy," Clinical Chemistry, vol. 27, No. 1, p. 33 (1981).

Tideman, A.M., "Clinical Evaluation of a Hospital Blood Glucose Monitoring System," Diabetes, May 1990, vol. 39, Supp. 1, The Program for the 50th Annual Meeting of the American Diabetes Association in Atlanta, Georgia, Abstract #877.

Tietz, N. (ed.), "Ektachem 700" in Textbook of Clinical Chemistry, (Philadelphia: W. B. Saunders Company) 1986, pp. 267–269.

Tietz, N.(ed.), "Methods for the Determination of Glucose in Body Fluids" in Fundamentals of Clinical Chemistry, (Philadelphia: W. B. Saunders Company) 1976, pp. 242–243.

TOA Technical Journal (1972) No. 3, pp. 2–9, "Royco–TOA Model 910 Cell Counter" (Japanese).

Toren, E.C. Jr., et al., "Interface Instrumentation between Computer and Spectrophotometer for Reaction Rate Measurements," Clinical Chemistry, vol. 16, No. 3, pp. 215–221 (1970).

Villeneuve, M.E. et al., "Evaluating Blood Glucose Monitors," American Journal of Nursing, Nov. 1985, pp. 1258–1259.

Walford, S. et al., "Self–Monitoring of Blood–Glucose—Improvement of Diabetic Control," The Lancet, pp. 732–735, Apr. 8, 1978.

Walker, E.A., et al., "What is the Present Practice of Quality Assurance for Bedside BGM in Health Care Facilities?," Diabetes, May 1990, vol. 39, Supp. 1, The Program for the 50th Annual Meeting of the American Diabetes Association in Atlanta, Georgia, Abstract #872.

Walter, B., "Dry Reagent Chemistries in Clinical Analysis," Analytical Chemistry, vol. 55, No. 4, Apr. 1983, pp. 498A–514A.

Wilkman, M.J., "Evaluation of Nurse Accuracy of Bedside Glucose Monitoring with Two Systems," Diabetes, May 1990, vol. 39, Supp. 1, The Program for the 50th Annual Meeting of the American Diabetes Association in Atlanta, Georgia, Abstract #682.

Wing, R.R., et al., "Behavioral Skills in Self–Monitoring of Blood Glucose: Relationship to Accuracy" Diabetes Care, vol. 9, No. 4, Jul., Aug. 1986, pp. 330–333.

Wylie–Rosett, J., et al., Brief Diabetes Quality Assurance (QA) Checklist,38 Diabetes, May 1990, vol. 39, Supp. 1, The Program for the 50th Annual Meeting of the American Diabetes Association in Atlanta, Georgia, Abstract #866.

Zamzow, K., et al., "New Wearable Continuous Blood Glucose Monitor (BGM) and Artificial Pancreas (A)," Diabetes, May 1990, vol. 39, Supp. 1, The Program for the 50th Annual Meeting of the American Diabetes Association in Atlanta, Georgia, Abstract #20.

Zimmet, P. et al., "Computerized Assessment of Self–Monitored Blood Glucose Results Using a Glucometer Reflectance Photometer with Memory and Microcomputer," Diabetes Research and Clinical Practice, pp. 55–63 (1985).

Zollinger, H., "The Mechanism of Oxidative Coupling," Azo and Diazo Chemistry Aliphatic and Aromatic Compounds, 1961, pp. 243–248.

* cited by examiner

DISTINGUISHING TEST TYPES THROUGH SPECTRAL ANALYSIS

DESCRIPTION OF THE INVENTION

1. Field of the Invention

The present invention relates generally to methods and apparatus for determining the test type to be performed on various types of test elements. More particularly, this invention provides methods for distinguishing between different types of test elements, including analytical test strips with fluid samples applied to them, analytical test strips with control solution applied to them, and standard strips as measured by a reflectance-type testing device.

2. Background of the Invention

Monitoring analytes such as glucose, cholesterol, intoxicants, and other constituents is frequently desirable in fluids, such as blood, plasma, blood serum, saliva, urine, and other biological fluids. In healthcare applications, such monitoring affords the opportunity to make rapid diagnoses of a patient's condition and to take prophylactic or therapeutic measures necessary for maintaining proper health.

One such healthcare application that has benefited tremendously by analyte monitoring in recent years is the treatment of diabetes. Diabetics suffer from an impaired ability to regulate glucose levels in their blood. As a result, diabetics can have abnormally high blood sugar levels known as hyperglycemia. Chronic hyperglycemia may lead to long-term complications such as cardiovascular disease and degeneration of the kidneys, retinas, blood vessels and the nervous system. To minimize the risk of such long term complications, diabetics must strictly monitor and manage their blood glucose levels.

Diabetics that have glucose levels that fluctuate several times throughout the day require very close blood glucose level monitoring. Close monitoring of blood glucose levels is most easily obtained when a diabetic is able to monitor their glucose levels themselves. Many devices currently available allow diabetics to measure their own blood sugar levels.

Reflectance-based monitors comprise one category of personal, or home-use, glucose level monitoring devices. These monitors utilize an optical block which accepts test elements for photometric analysis.

The test elements are usually in the form of test strips, which contain analytical chemistry. Conventionally, these test strips are in the form of a disposable diagnostic test strip containing analytical chemistry upon which a fluid sample is deposited. Once the user applies the fluid sample to the test strip, and the sample has sufficiently penetrated the test strip, a chemical reaction occurs in the presence of a target analyte, e.g., glucose, to cause a change in the optical properties of the test strip. An optical photometric device then determines the analyte level of the sample by measuring an optical property, such as the intensity of reflected light at a certain wavelength from the test strip. For in vitro analysis in healthcare applications, the fluid sample is usually fresh whole blood. Periodically, however, it is desirable to run a test on a test element formed by applying a control solution of known analyte concentration to a test strip, in order to verify that the meter is performing within operational limits. It is also desirable for the user to insert a "standard strip", which is a test element that has known optical properties, in order to verify that the meter is operating within operational limits.

Diagnostic test strips for testing analytes such as glucose levels of blood samples are well known in the art and comprise various structures and materials. Test strips typically include single or multi-layered porous membrane arrangements which receive a blood sample and undergo a change in an optical property, such as a color change, in response to the interaction of blood glucose with agents/reactants in the membrane. Examples of such multi-layer strips are described in U.S. Pat. Nos. 5,296,192 to Carroll and 6,010,999 to Carroll et al., the contents of both of which are incorporated herein by reference.

Prior to reaching the reactants, a whole blood sample can be filtered to eliminate potential optical interference by removing erythrocytes, or red blood cells. Some test strips operate to allow the applied blood sample to migrate to a reaction site in the membrane where the sample reacts with the agents/reactants, which is located in downstream capillary relation to the sample application site. The results of the reaction are often visible as a color change at the reaction site. However, the change may occur in invisible regions of the electromagnetic spectrum, such as infrared and ultraviolet. For the purposes of this application, the term "color change" will be understood to include variations in optical properties throughout the visible and invisible regions of the electromagnetic spectrum. As noted above, a color change can be correlated to the amount of glucose in the sample. Home-use glucose measuring devices that use a reflectance meter to measure the color change of the test strip correlate glucose levels to the change in the amount of light reflected from the reaction site of the test strip. As is well known in the art, strips can be formulated to produce a color change within a certain spectral region, and the meter designed to photometrically measure reflected, absorbed or transmitted light at a wavelength sensitive to the color change of the strip. While the present invention will be described with reference to reflectance based photometry, it would be known to one having ordinary skill in the art to apply the features of the invention to absorbance or transmittance based systems.

Desirable for maintaining the accuracy of blood glucose monitoring devices is the periodic checking of the device to ensure that it is within operational compliance. As mentioned above, certain periodic standardization tests performed by the user provide verification of the meter's accurate operation. Accuracy is required by regulatory authorities for medical devices such as diabetes testing monitors, where a patient's life can depend on proper operation of the monitoring system.

Common verification techniques are designed to periodically check whether the monitoring device is operating properly, and thus accurately measuring blood glucose levels. Verification techniques used in glucose level monitoring devices include inserting test elements having a known glucose or reflectance value into the monitoring unit and comparing the measured results with the known values. Test elements having known glucose levels ("Control Test Elements" hereinafter) are normally prepared by applying a glucose control solution having a known glucose concentration to a dry test strip that normally could be used to run a test with blood. The control test element is then inserted into the monitoring unit and a test is performed and the calculated glucose value of the test element is displayed. The calculated glucose value is then compared with a range of acceptable results provided by the manufacturer for the glucose control solution. If the results displayed by the device for the control test element fall with an acceptable range designated for the solution, the device is deemed to be appropriately functioning ready for testing a blood sample.

Another verification technique commonly used in glucose level monitoring devices includes inserting a strip with a known reflectance value into the monitoring unit ("Standard Test Element" of "Standard Strip" hereinafter). This standard test element does not receive a fluid sample, but is rather formed of a one piece rigid or semi-rigid material such as plastic having known optical properties. The standard reflectance strip can be stored in a compartment of the monitoring unit so that it is conveniently available for use throughout the life of the monitoring device. The standard reflectance strip is inserted into and measured by the device just as other test strips, and the measurement results are compared with a range of acceptable results provided with standard reflectance strip. As with the test using the glucose control test element, if the results of the measurement fall within an acceptable range, the device is ready for testing a blood sample.

The test run with the standard test element ("Standard Test" hereinafter) is intended to test the performance of the monitoring device only, while the test run with the control test element ("Control Test" hereinafter) is intended to check the entire monitoring process including the testing technique of the user. Conventional glucose monitoring devices are capable of performing both types of calibration techniques and will normally include instructions regarding when to initiate each type of calibration technique.

Of course, the monitoring device must also accept a test element formed by sample fluid, such as blood, applied to a test strip ("Analytical Test Element" hereinafter), and run an analytical test thereon to determine analyte concentration ("Analytical Test" hereinafter).

A problem with prior art devices has been that they have typically not been able to discriminate between the type of test element introduced into the meter, and therefore the type of test to run, without user intervention. For example, the standard test is instantaneous and need not ascertain that a reaction on a test strip has run to completion, as is required in the control test and the analytical test. It is also desirable that the historical results for all three tests should be stored separately, so that the user's results from the analytical tests are not mixed in or displayed with the standard test or control test results.

Conventional methods for differentiating the test type have required the user to perform an affirmative act, such as pressing a button on the device, to signal to the device that the test strip inserted includes a glucose control solution and not a blood sample.

The requirement that a user perform an affirmative act to signal to the monitoring device the type of sample tested allows the possibility for human error that can adversely affect the proper storing and monitoring of measurement results, and possibly the misinterpretation of stored results. For example, if a user were to fail to perform a required step indicating insertion of a test strip containing glucose control solution, such as failing to push a button or wait a specified time, the measurement results could be incorrectly stored in the memory of the device as an actual blood glucose level result, possibly resulting in, among others, false self-diagnosis of blood sugar levels or erroneous treatment regimens being prescribed by healthcare professionals.

Another prior art system is a "negative blood" approach, which uses two wavelengths. In such a system, a secondary LED which measures at a wavelength at which red blood cells are highly detectable. This measurement is used to formulate a correction factor used in running the glucose test in whole blood to subtract out optical interference caused by hemoglobin. This arrangement is usually necessary in conjunction with single-layer test strips, which are generally unable to adequately separate hemoglobin from whole blood sample as it flows to the opposite surface where the colorimetric reaction with the reagent is desired to be measured. If reflection from this secondary LED is not detected to achieve a certain threshold, that is if there is no hemoglobin detected, the meter automatically assumes that the test element is a control element. This methodology is in essence binary, and is limited to the distinction between "Blood" and "Not Blood," and is therefore not satisfactory if there are more than two possibilities.

The difficulties monitoring devices have in properly distinguishing the type of test element inserted also carries over to distinguishing between insertion of a test strip having a sample applied thereon, i.e. a control test element or an analytical test element, and insertion of a standard reflectance strip. Again, conventional monitoring devices have the drawback of requiring an affirmative act from the user to signal that a non-analytical test is being performed by the monitoring device. It is accordingly an object of the invention to provide a method for automatically distinguishing between the type of test performed by the device based on the test element inserted by the user, without the need for any affirmative act by the user.

SUMMARY OF THE INVENTION

In accordance with the invention, a method for automatically selecting test types in an analytical meter system is described, the method comprising the steps of:

providing a test element, said test element belonging to one of a plurality of test element types;

inserting said test element into an analytical meter system;

measuring a first optical property of the test element;

measuring a second optical property of the test element;

distinguishing said test element by identifying a predetermined relationship between said first and second optical properties;

selecting a test type based at least in part upon the results of said distinguishing step.

Also described is a meter system for performing one of a plurality of test types on a test element, where the test element is inserted into the meter system and belongs to one of a plurality of test element types, the meter system comprising:

a first light emitting diode selectively discharging light at a first wavelength;

a second light emitting diode selectively discharging light at a second wavelength;

at least one light detector for measuring light emitted from the first and second light emitting diodes and reflected from a test element; and a processor for distinguishing said test element by identifying a predetermined relationship between first and second optical properties, and further for selecting a test type based at least in part upon the results of said distinguishing.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and, together with the description, serve to explain the principles of the invention.

DETAILED DESCRIPTION OF THE INVENTION

Reference will now be made in detail to an illustrative embodiment of the invention, which appears in the accompanying drawings. Wherever possible, the same reference numbers will be used throughout the drawings to refer to the same or like parts.

Figure 1:
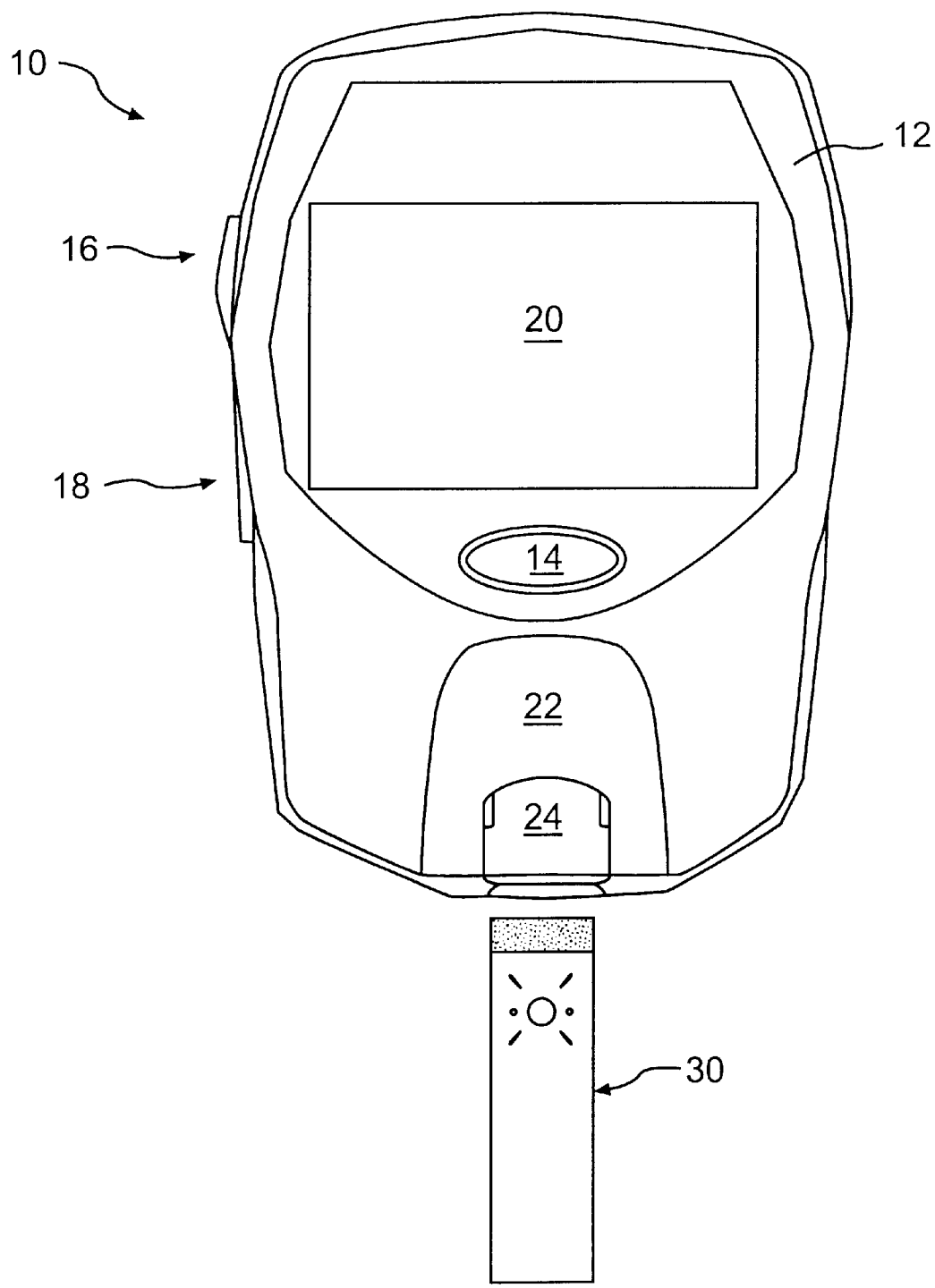
FIG. 1 illustrates an analyte meter system according to the present invention.

With reference to the drawings, FIG. 1 depicts an analyte meter system 10 according to the present invention. Meter system 10 generally includes a hand-held meter having a housing enclosure 12, power button 14, control buttons 16, 18, liquid crystal display (LCD) 20, removable test chamber cover or shroud 22 having a test strip platform 24 for receiving and testing a multi-layered diagnostic test strip 30. A strip sensor (not shown) of known configuration is located at a distal end of the strip platform 24 to detect when a test strip 30 has been fully inserted into the device. The test strip 30 contains a reagent that produces a detectable response in proportion to the amount of a suspected analyte, such as glucose, cholesterol, ketones, theophylline, and fructosamine, and others. Although the present invention is adaptable for testing multiple analytes, discussion is directed herein to monitoring glucose levels in whole blood samples for purposes of describing the instant invention.

Figure 2:
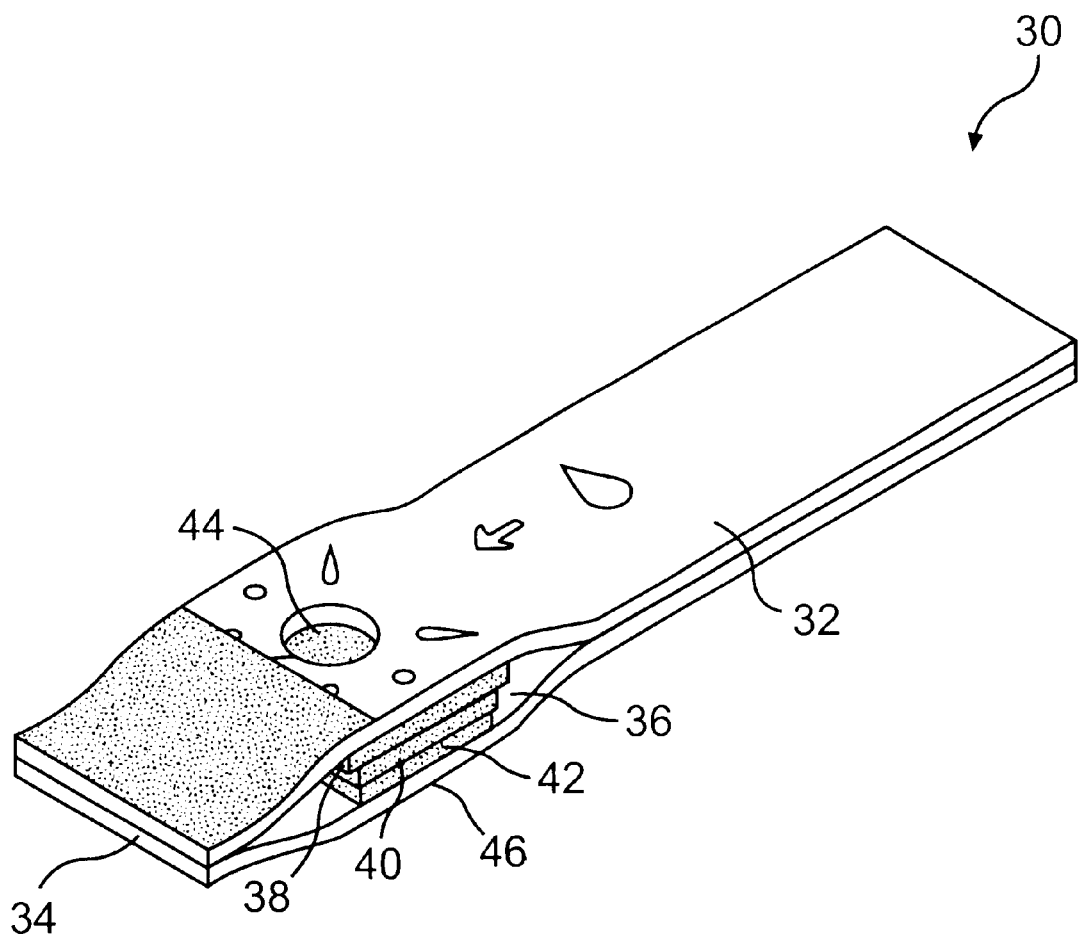
FIG. 2 illustrates a test strip for receiving a fluid sample and insertion into the meter system of FIG. 1, all in accordance with the present invention.

FIG. 2 illustrates an enlarged view of diagnostic test strip 30. Test strip 30 generally includes an upper and lower support layer 32, 34, with sample receiving layers 36 located between the support layers 32, 34. Sample receiving layers 36 include a spreading layer 38 located adjacent upper support layer 32, a separating layer 40, and a semi-porous membrane reagent layer 42 located adjacent lower support layer 34. At least one of the sample receiving layers 36 is pretreated with a dry chemistry reagent and conditioning solution. Preferably, the membrane 42 and separating layer 40 are pretreated with the reagent/conditioning solution. The spreading layer 38 may also be treated. Each layer is positioned in substantially continuous contact with its adjacent layer as shown in FIG. 2 by adhesives and ultrasonic bonding, or other known means, to provide a sealed composite structure.

The top and bottom support layers 32, 34 of test strip 30 each define an aperture or opening therethrough. These apertures or openings of the test strip 30 are oriented in vertical alignment with a test window (not shown) located along strip platform 24 (FIG. 1) when properly positioned in meter system 10. The opening in the upper support strip 32 defines a sample receiving port 44 and the opening in the lower support strip 34 defines a reaction viewing port 46. The sample receiving layers 36 are oriented in vertical alignment with sample receiving port 44 and reaction viewing port 46. This allows the blood sample received by the test strip 30 to pass directly from receiving port 44 to viewing port 46. As the sample travels to the viewing port 46 it will encounter reagent, and any analyte in the sample will begin to react with the reagent and begin to form an optically detectable condition, such as a color change. This optically detectable condition is assessed from the viewing port 46, and can be used to determine the presence of, or calculate the concentration of an analyte of interest. The test strip 30 of FIG. 2 is illustrative only and many other test strip configurations may be used when practicing the present invention.

Figure 5:
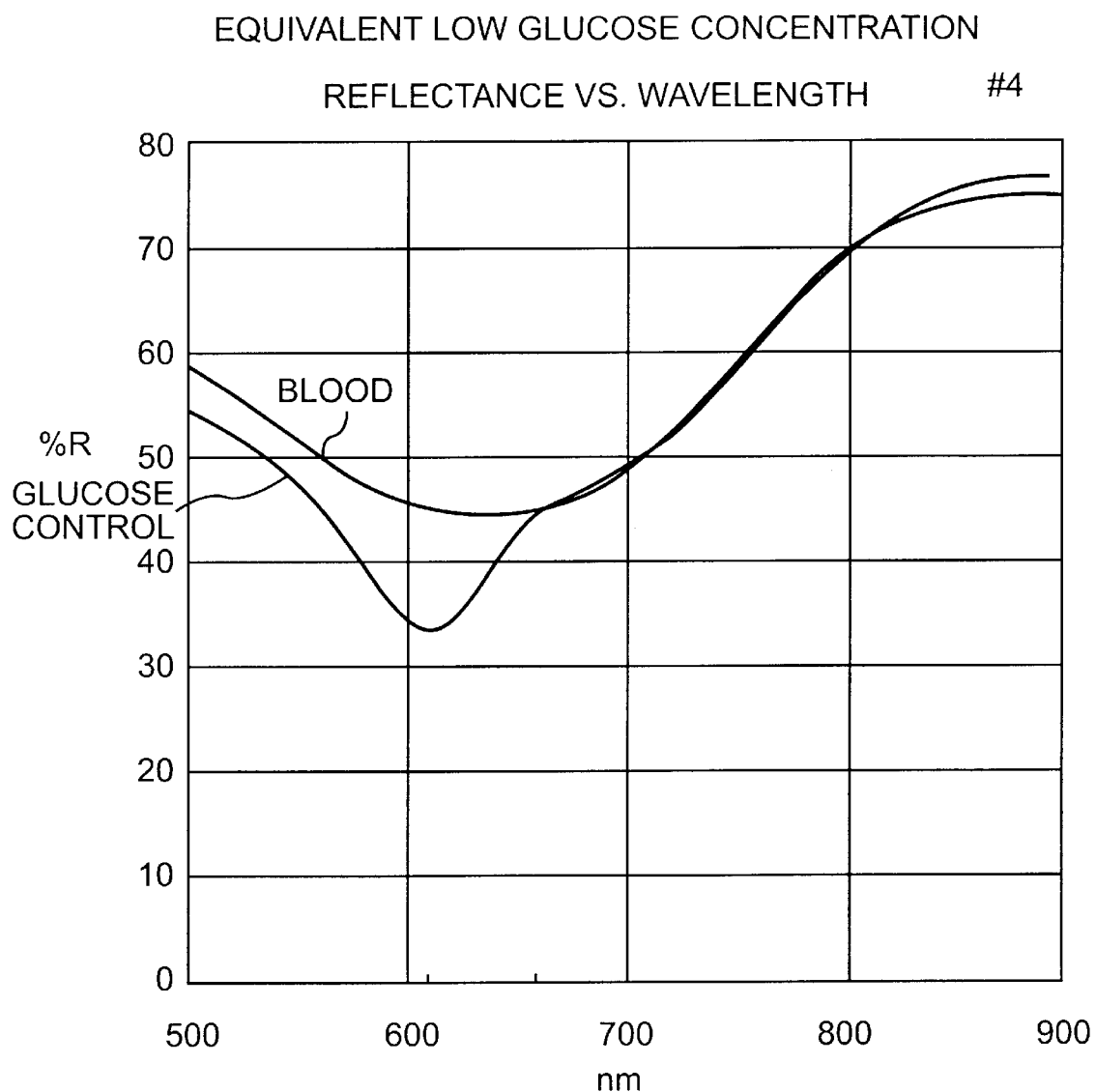
FIG. 5 illustrates a graph of Reflectance v. Wavelength comparing the spectral curve of an analytical element formed of blood sample of relatively low glucose concentration applied to the test strip of FIG. 2, with that of a control element formed of control solution of substantially equal glucose concentration applied to the test strip of FIG. 2.
Figure 6:
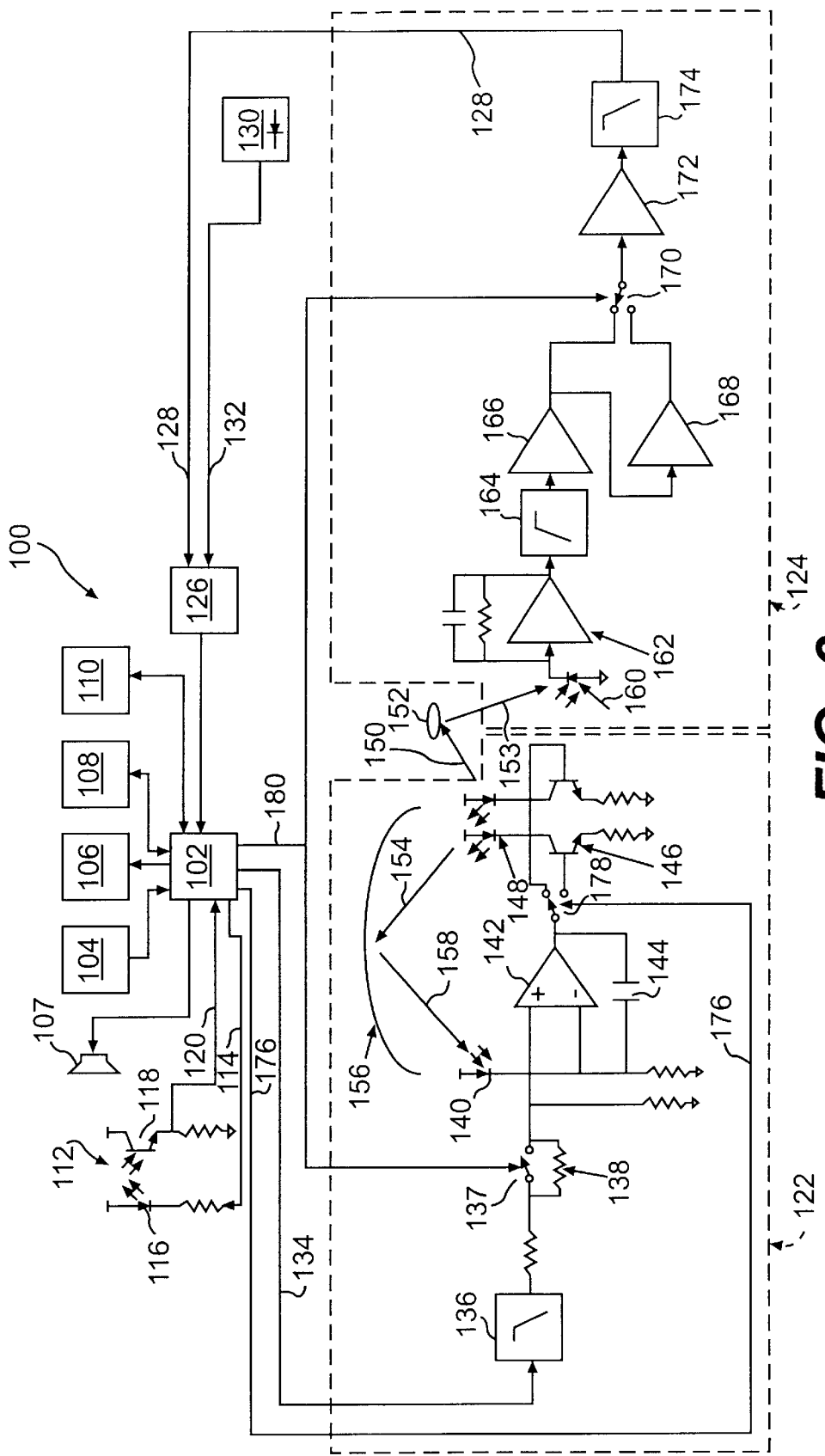
FIG. 6 is a schematic representation of a meter system according to the present invention.

Monitoring meter system 10 of the present invention includes a circuit assembly physically and electrically connected to a printed circuit board, an example of which is schematically depicted as the block diagram of FIG. 5. The circuit 100 contains a microprocessor 102 with a plurality of inputs and outputs. An exemplary embodiment of the present invention uses an 8-bit device with 60 K of programmable memory. The microprocessor executes the meter instruction code. The microprocessor receives input from the user through input device 104, which can include buttons or other input devices known in the art. A display 106 and a sounder 107 or similar output devices receives data from the microprocessor for presentation to the user. A memory device 108, for example EEPROM, is also connected for input from and output to the microprocessor 102. A communication port 110 can also connected in input-output relationship with the microprocessor in known manner.

A strip sensor 112 receives a drive signal through line 114 to turn on and off photo element 116. The photo element can be an LED. Light from the photo element 116 is detected by the photodector 118. The photodetector can be a photodiode or phototransistor. Output from the photodetector is supplied via line 120 to the microprocessor 102. The strip sensor detects when a strip is inserted into the meter, and can be initialized by the method described in commonly assigned, copending U.S. patent application Ser. No. 09/794,037 (entitled "Improved Method of Strip Insertion Detection"), filed concurrently herewith, the contents of which are incorporated herein by reference.

The circuit assembly can include a light intensity control circuit, represented as section 122 of the diagram, and a light detector circuit 124, discussed in further detail hereinbelow. An exemplary embodiment of the present invention operates using a DC offset ("virtual ground") of 2.5 V reference (not shown) and is powered from a 1.5 V AAA battery (not shown), which may include a voltage divider circuit or other power management circuitry as is known in the art.

An analog to digital (A/D) converter 126 converts analog electrical output on line 128 from the light detector circuit 124 into digital information for the microprocessor 102. In an exemplary embodiment of the invention, a 12-bit A/D converter is employed. A temperature sensor 130 provides a voltage proportional to the temperature along line 132 to the A/D converter. The microprocessor 102 can make a determination as to whether the temperature of the testing environment is within predetermined thresholds, and prohibit a user from running a test if accuracy would be negatively affected.

The light intensity control circuit (LICC) 122 will now be described. In an exemplary embodiment, the circuit is supplied by a pulse width modulated signal along line 134 from the microprocessor 102. The circuit includes a low pass filter 136, a modulator 137, a flux biasing resistor 138, a reference photodiode 140, a control loop error amplifier 142, a feedback loop compensation capacitor 144, and LED drive transistors 146. The LICC controls the drive supplied to the LEDs 148, as will be described.

The LEDs, of which there are two in the exemplary embodiment, generate light, a component 150 of which will encounter the target 152, which is the test strip or other test element inserted into the meter. Another component 154 of the light strikes a chamber reflector 156 and a portion of which 158 is reflected toward reference photodiode 140. One of the LEDs is a 660 nm LED in the exemplary embodiment, which is appropriate for detecting glucose in a test strip marketed under the tradename PRESTIGE and sold by Home Diagnostics, Inc. of Ft. Lauderdale, Fla. The exemplary embodiment can be easily modified for detecting other analytes or using other strips by changing the software and LED used to obtain a different wavelength. For instance, a 580 nm LED would be preferred for ketones using known analytical chemistry systems.

The light detector circuit (LDC) 124 will now be described. In an exemplary embodiment, the LDC includes a main photodiode 160, a transimpedance (current to voltage) amplifier 162, a high pass filter 164, an amplifier 166, and a negative gain amplifier 168. The output stage of the exemplary LDC includes a demodulator 170, a level shifting amplifier 172, and a low pass filter 174. The output stage provides a DC voltage to line 128, as set forth above. The LDC supplies an analog signal to the A/D converter, which when digitized is interpreted by the microprocessor to provide test results.

In the exemplary embodiment, input to the A/D converter is conventionally multiplexed, receiving input from lines 128 and 132, and from other signal lines not shown and not necessary to understand the present invention.

In the exemplary embodiment, two LEDs are employed, at 610 nm and 660 nm as described herein. The LEDs are selected according to the instruction code at appropriate times by the microprocessor 102 by a signal sent via line 176, which activates a switch 178. If additional LEDs are employed, then additional signal lines and switches can be added in conventional manner.

The operation of the exemplary circuit 100 will now be described. A pulse width signal is produced by the microprocessor 102 along line 134. As is well known, the pulse width modulation signal is basically a 2.5 V signal delivered either on or off according to a duty cycle. In a perfect square wave, the duty cycle is 50%, so that the signal is 50% on, and 50% off. Accordingly, when the signal is on, it is delivered at 2.5 volts and when it's off, it is zero volts. The signal in line 134 is averaged by the low pass filter 136 to arrive at a drive voltage for the LEDs, which will in turn determine their output. For example, for a perfect 2.5 V square wave, the average voltage, and thus the output of the low pass filter 136 will be 1.25 V. In this way, the power delivered to the LEDs can be modified by the microprocessor by changing the duty cycle of the pulse width modulation signal. To increase the light power, the duty cycle of the signal would be increased.

In the exemplary embodiment, the duty cycle of the pulse width modulation signal is determined during factory calibration of the meter, and the duty cycle value is permanently stored in the EEPROM. Of course, periodic calibration routines known in the art could also be employed. Further, different LEDs may have different preferred drive requirements, so different duty cycles can be utilized based on the LED in operation.

The circuit 100 employs a modulation or "chopping" function controlled by the microprocessor 102. The microprocessor 102 supplies a modulation signal via line 180 to the modulator 137 of the LICC and to the demodulator 170 of the LDC in synchrony. The chopping signal is essentially a square wave (on/off) signal supplied to drive the LEDs at a certain frequency, rather than at constant power, to eliminate noise in the signal output of the circuit. In the exemplary embodiment, a 2 kHz chop is employed. The chopping function allows the shifting of the frequency of the light signals LICC upward to a "quieter" region of the spectrum where ambient light effects can be minimized in the LDC. For example, while sunlight is 0 Hz (DC), incandescent lights have a frequency of 120 Hz. Fluorescent lights are also 120 Hz, but also have harmonic frequencies. By shifting the drive frequency of the LEDs above that of ambient light at the LICC, the LDC will be able to receive a signal at the matching frequency that is above the spectrum where most noise is encountered.

The LICC includes flux biasing resistor 138 which is in parallel with modulator 137. This resistor in parallel essentially inhibits the voltage from the low pass filter 136 from being completely turned off by the modulator 137. In this way, the chopping function, instead of modulating between full-on to full-off will modulate between full-on and low. The result is that the LEDs will be either full-on or dim, but never completely off. Several benefits are realized by this arrangement. First, because the LEDs are never dark, a positive bias is always present at the reference diode 140. As a result, when interfering ambient light reaches the reference diode 140, there is a tendency for the modulated signal to move toward ground. This positive bias helps to compensate for this tendency toward ground and allows the circuit to adapt without a change in peak-to-peak amplitude by keeping the modulated signal above ground. Second, the fact that a voltage is always present maintains control loop error amplifier 142 further above ground, which promotes better performance.

The control loop amplifier 142, in connection with the compensation capacitor 144 receives the output from the reference photodiode 140 to provide a feedback mechanism in determining the appropriate drive power for the LEDs 148.

When target 152 is illuminated by light 150 from an LED 148, reflected light 153 is received by the main photodiode 160, producing a photocurrent based on the reflectance. The photocurrent output of the photodiode 160 is supplied to transimpedance amplifier 162, which converts the photocurrent to a voltage. This voltage is conditioned by high pass filter 164, which removes noise components of the signal below the chopping frequency. It is here that the noise components of artificial lighting are filtered out, although certain harmonics of fluorescent light are eliminated after demodulation by low pass filter 174. In the exemplary embodiment, a 400 Hz cutoff frequency is employed in high pass filter 164.

The signal emerging from high pass filter 164 is basically a square wave voltage at the chopping frequency that is nominally 0.5 V peak to peak maximum and centered about the virtual ground of 2.5 V. To condition the output for the A/D converter, which in the exemplary embodiment operates at approximately 2.6 V maximum, amplifier 166 and negative gain amplifier 168 are employed as follows. When the LED is on, the top half of the square wave is connected by level shifting amplifier 172; and when the LED is off, the bottom half of the square wave is amplified by minus unity and connected by level shifting amplifier 172. This inverts the bottom half of the square wave when the LED is off. The demodulator 170 selects between the amplifiers 166, 168 in synchrony with the modulation occurring in the LIDC at modulator 137. The resulting signal emerging from demodulator 170 is a DC signal proportional to the reflectance of the chemistry, in relation to the 2.5 V reference voltage in the exemplary embodiment.

Level shifting amplifier 172, a differential amplifier, receives the DC signal from the demodulator 170, applies a gain and shifts the signal to a range acceptable to the A/D converter, which in the exemplary embodiment is approximately 2.6 V maximum. Low pass filter 174 removes spiking introduced by the demodulation of the signal by amplifiers 166, 168, and also removes a large amount of the harmonics of artificial light that were shifted high by the demodulation. Further, Any DC offsets in the amplifier stages prior to the demodulations that were shifted up to the chopping frequency are also effectively filtered. The only noise left in the signal are harmonics of ambient light that are right around the chopping frequency, which in the exemplary embodiment of 2 kHz are minimal.

These remaining harmonics are of known frequency and their relationship to the chop frequency will determine their frequency. For example, the $17^{th}$ harmonic of fluorescent lighting will be 120 Hz×17=2040 Hz. If the chop frequency is 2048 HZ, which is more conveniently generated by binary digital systems than 2000 Hz, the strongest remaining interfering harmonic will be 8 Hz (|2048 Hz−2040 Hz|). Since this interfering signal is of known frequency, it can be further reduced by simple synchronous digital filtering techniques. In countries that use 50 Hz power grids, the strongest interfering frequency will be 2 Hz (the $25^{th}$ harmonic of 100 Hz=2050 Hz, |2048 Hz−2050 Hz|=2 Hz). A simple synchronous digital filtering technique that "nulls-out" both 2 Hz and 8 Hz can be implemented.

Testing fluid samples for glucose levels according the present invention generally includes insertion of test strip 30 containing a blood sample into meter system 10 within test chamber cover 22 along strip platform 24. Proper insertion of the test strip 30 in meter system 10 results in locating the reaction viewing port 46 of the test strip 30 directly above the test window (not shown) of meter system 10. Once the test strip is properly inserted in meter system 10, the 660 nm LED discharges against viewing port 46 of test strip 30, and the reflectance from the discharge is registered by one or more light detectors. This process continues until the motor system, according to an algorithm, calculates the glucose level of the sample. A representative algorithm is described in commonly-assigned copending U.S. patent application Ser. No. 09/794,045 (entitled "Method for Determining the Concentration of an Analyte on a Test Strip"), simultaneously filed herewith, the contents of which are incorporated herein by reference.

The microprocessor and algorithm software of meter system 10 perform calculations to arrive at the ultimate glucose measurement. It should be noted, however, that similar calculations may be used for deriving the amount of other analytes found in the test strip 30 so long as meter system 10 has been properly reconfigured and calibrated for the particular analyte of interest.

Meter system 10 according to an illustrative embodiment of the invention is intended to receive and automatically differentiate between at least three different types of test elements, as discussed hereinabove. The three types of tests include: (1) an analytical test; (2) a control test; and (3) a standard test. To avoid combining different types of test results, the results of each test type can be stored in separate locations in the memory of meter system 10. This categorizing of the test results would allow for separate recalling of test results for each type of test, but would not combine results from different types of tests. Access to different types of test results could also be determined by different protocols, for example allowing a user to view historical analytical test results, but limiting access to historical standard test results to service technicians. Alternatively, only the results of certain types of tests could be saved, and others not saved.

The present invention automatically differentiates between the three different types of tests by analyzing aspects of the spectral curve derived from reflectance measurements taken from a test element inserted into the meter system. Aspects of the spectral curve associated with an inserted test element can be ascertained by analyzing the percentage of reflectance of the test strip measured over certain predetermined wavelengths, or a range of wavelengths. An example of a spectral curve for an analytical element, using whole blood to test for glucose, according to the present invention and measured between a wavelength range of 500 nm to 900 nm is illustrated in FIG. 3.

Figure 3:
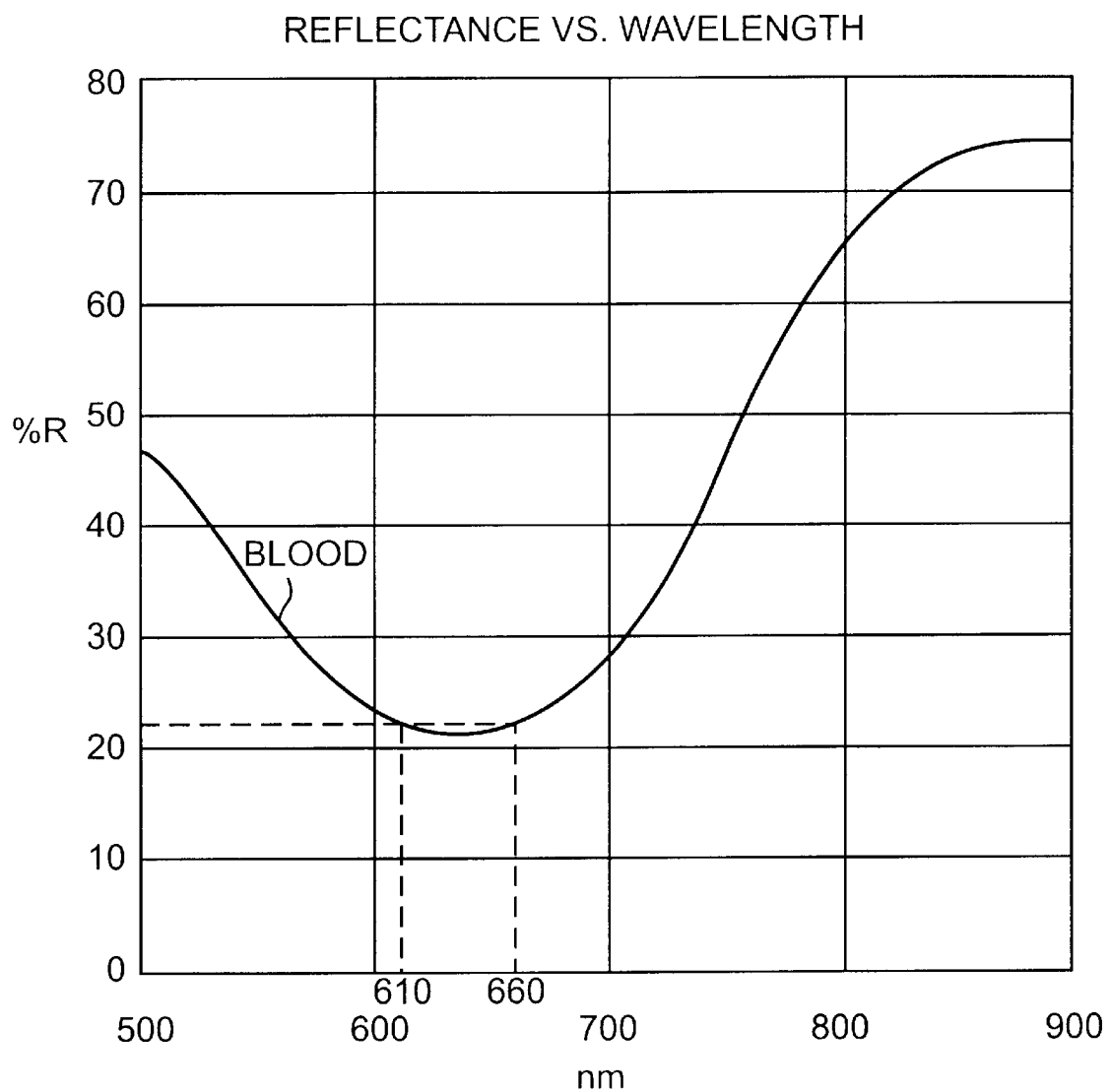
FIG. 3 illustrates a graph of Reflectance v. Wavelength for an analytical element formed of blood sample of relatively high glucose concentration applied to the test strip of FIG. 2.

As illustrated in FIG. 3, the spectral curve of the blood sample forms a generally concave shape between a wavelength range of 500 nm to 800 nm, with the lowest portion of the curve located generally between a wavelength range of 600 to 700 nm. It has been found that all blood samples applied to the type of test strip described above, and measured in the manner described above, provide a spectral curve resembling the that shown in FIG. 3. While the shape of the spectral curve remains similar for all blood samples irrespective of glucose concentration (Cf. FIG. 5), especially within the range of 600 nm to 700 nm, the actual reflectance percentages may vary from blood sample to blood sample. For example, the spectral curve shown in FIG. 3 corresponds to a blood sample having a high glucose concentration on a PRESTIGE brand test strip, as depicted by the lowest portion of the curve indicating a 20 to 30 percent reflectance. Alternatively, the spectral curve for a blood sample having a low glucose concentration as shown in FIG. 5 will still have its lowest point between the wavelength range of 600 to 700 nm, but with a percentage reflectance above 40.

This vertical displacement of the entire spectral curve for blood glucose tests presents challenges in differentiating test types, because absolute thresholds are not easily applied.

As described above, the illustrative embodiment uses a 660 nm wavelength LED to measure reflectance of a test element inserted into meter system 10. This wavelength has been selected based on numerous factors, including system components and type of test strip used, and is designed to correspond with a peak optical response, e.g., absorbance, of the reaction of analyte with reagent on the test strip. While the illustrative embodiment contemplates measuring reflectance with a LED having a wavelength of 660 nm, it is within the scope of the invention that any other wavelength could be used in association with a different test strip composition or system components.

Looking again at the spectral curve of the blood sample of FIG. 3, there is described the optical response over a range of wavelengths for a high glucose sample applied to a test strip as described by the Carroll patents. Such strips are commercially available from Home Diagnostics, Inc., of Ft. Lauderdale, Fla., under the trademark PRESTIGE SMART SYSTEM. For this glucose reagent system, the reflectance percentage value (% R) measured at a wavelength of 660 nm is approximately the same as the reflectance percentage value measured at a wavelength of approximately 610 nm. It was noted by the present inventors that, because as noted above, the shape of the spectral curve for blood is substantially similar irrespective of glucose level, every blood sample tested will return similar reflectance percentage values at approximately 610 nm and approximately 660 nm. Although the absolute value of the % R reading would vary with glucose concentration, the % R measurements at 610 nm and 660 nm would always be very nearly the same.

When using a chromogen as an analyte indicator such as with known dry chemistry test strips, the Kubelka-Munk K/S reflectance values can be used to draw a predictable quantitative relationship between color development and concentration of the analyte. The spectral curve of the glucose reaction on a given test strip that is measured is of a known shape and it is known that glucose concentrations can be calculated using K/S values. The effects of intentionally distorting the spectral curve shape of the reaction by adding a dye to the glucose control solution can also be measured using K/S, specifically the difference in K/S values at two different wavelengths. Therefore, K/S can be used to measure the spectral curve shape of both a blood glucose and glucose control reaction.

The advantage of using K/S values instead of raw % R in calculations is that using K/S values tend to provide a more consistent method of measurement from varying lots of chemistry strips, which vary from lot to lot. The advantage of using % R is that it tends to provide a more consistent method of measuring the effect of the dye in the glucose control solution. As a general proposition, it is easier to control the amount of dye in the glucose control from lot to lot than it is to control the optical properties of strips from lot to lot. As a result, K/S can be a more robust means of measuring the differences in the spectral curve shape from chemistry lot to chemistry lot. However, in some circumstances, Δ% R may hold a slight advantage over delta K/S, for example when measuring low glucose concentrations.

The use of K/S values in an exemplary practice of the present invention is described in the examples below, where Ch1 is 660 nm, and Ch2 is 610 nm.

EXAMPLE 1

% R Method (Glucose Control Detection Using Reflectance)

Glucose Control detected when Ch2 % R is at least 3.5% R less the Ch1 % R at the conclusion of the test.[1]

[1]Actual % R cutoff value varies with dyes, chromogens and wavelengths used.

Pseudo Code
If Ch2 % R<=Ch1 % R−3.5% R Then
   Glucose Control sample detected
Else
   Blood sample detected

EXAMPLE 2

K/S Method (Glucose Control Detection Using K/S)

Glucose Control detected when Ch2 K/S is at least $0.3^2$ less that Ch1 K/S at the conclusion of the test.

[2]Actual K/S cutoff value varies with dyes, chromogens and wavelengths used.

Pseudo Code
If Ch2 K/S<=Ch1 K/S−0.3 Then
   Glucose Control sample detected
Else
   Blood sample detected

EXAMPLE

Gating (Control Detection with Glucose Level Gating)

Glucose control solutions are manufactured at known glucose concentrations. Certain glucose concentrations can immediately be excluded from the need for spectral analysis by glucose concentration level alone. For example, blood detection is indicated, but when final glucose value exceeds 400 mg/dL, control solution is identified. In this case, no spectral curve shape analysis would be required.

Pseudo Code
If Final Glucose>400 mg/dL Then
   Blood sample detected
Else
   Spectral curve shape must be analyzed to determine sample type In accordance with an illustrative embodiment of this invention, and as described above, meter system 10 incorporates a second LED having a wavelength of 610 nm. The second LED operates to measure a second point along the spectral curve of the test element inserted into the meter. It is this second LED, acting in conjunction with the strip sensor, that allows the meter system according to the illustrative embodiment to automatically differentiate between at least the three different types of tests described hereinabove to be conducted by meter system 10. The three types of tests are the analytical test, the standard test, and the control test.

In performing the standard test, a standard strip is inserted into the meter. This standard strip, as is known in the art, can be formed with a notch in the distal end (the end first inserted into the meter) so as not to trip the strip sensor upon full insertion. When inserted, the meter optics will detect the presence of the standard strip because reflectance values increase (with no test element in place, reflectance is, corrected for ambient light and noise, statistically equal to zero). Because the strip sensor will not indicate presence of a test strip because the notch on the standard strip will not trip the strip sensor, the meter will be able to ascertain that the test element inserted is the standard test element, and the test run is the standard test.

If the strip sensor is triggered, however, then the meter system will know that a test strip has been inserted. The test strip is common to both the analytical element and the control element. Distinguishing between the two, and thus between an actual blood sample and a glucose control solution, is facilitated by incorporating a dye within the glucose control solution that alters or distorts the spectral curve, or shape, of the control element. The dye preferably has a narrow spectral absorbance so that it does not significantly impact the glucose evaluation of the sample. The distortion of the spectral curve of the control element due to the dye provides a substantially different reflectance percentage value measured at 610 nm relative to that at 660 nm. As described above, the % R values returned at these two wavelengths are very nearly the same in blood. Accordingly, meter system 10 ascertains that a standardization and verification test using glucose control solution is being conducted when the reflectance percentage values using the 610 nm LED is measurably different relative to the 660 nm LED when the strip sensor is tripped. The amount of difference between reflectance percentage values between the 610 nm channel and the 660 nm channel is dependent on the type and amount of dye incorporated into the glucose control solution. The type and amount of dye used should be selected so that it does not exhibit significant absorbance at 660 nm. For example, a dye causing a six point absolute difference in reflectance percentage values between measurements by the two LEDs has been found sufficient to consistently and accurately distinguish the control solution from a blood sample. Because the dye affects the shape of the curve, the absolute reflectance measurement is not what is important. What is important is the relative difference between the reflectance percentages returned between the two wavelengths, which difference would remain substantially constant irrespective of the absolute values.

Figure 4:
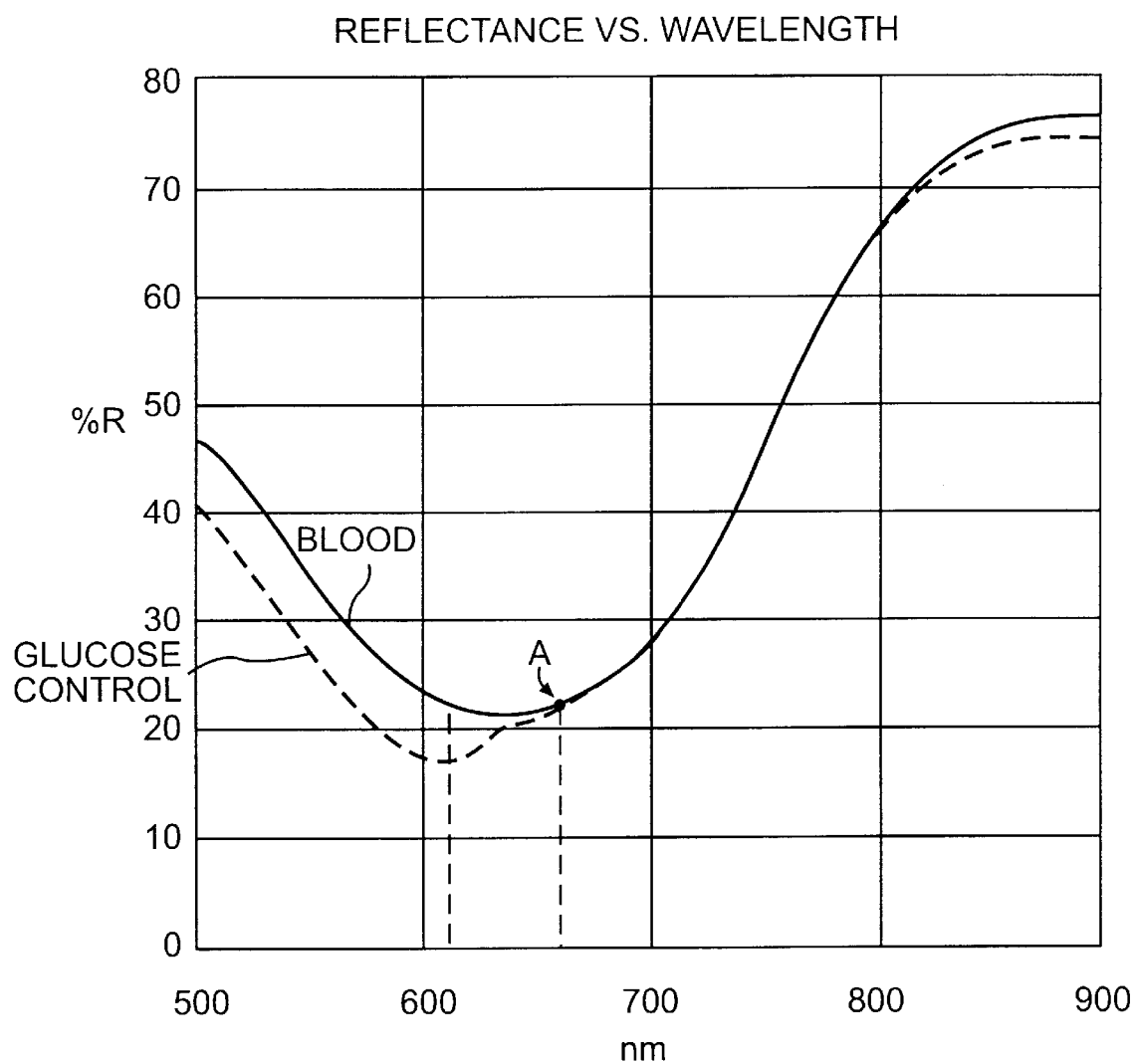
FIG. 4 illustrates a graph of Reflectance v. Wavelength comparing the spectral curve of the analytical element of FIG. 3 with that of a control element formed of control solution of substantially equal glucose concentration applied to the test strip of FIG. 2.

FIG. 4 depicts a graph of Percentage Reflectance v. Wavelength comparing the spectral curve of the blood sample of FIG. 3 (shown in a solid line) with a spectral curve of a glucose control solution with dye (shown in a dashed line) in accordance with the present invention. To highlight the method for distinguishing between the samples, the samples illustrated in the graph have approximately the same glucose concentration. This is evident from the measured percentage reflectance being approximately the same for both samples using the 660 nm LED. See point A of the graph of FIG. 4.

As indicated in the graph of FIG. 4 and described above, the spectral curve for the analytical element (blood) has approximately the same percentage reflectance value when measured using both the 610 nm and 660 nm wavelength LED. The spectral curve for the control element (control solution with the added dye), however, contains a deflection such that the reflectance percentage value at 610 nm is approximately six units lower than the reflectance percentage value obtained with a 660 nm LED. Based on this deflection of the spectral curve resulting from the dye, meter system 10 can be programmed to distinguish between an analytical element and a control element, and thus properly select the appropriate test, data processing protocols, display, and related protocols.

In accordance with the invention, any suitable dye can be used to modify the spectral curve of the glucose control solution, as long as it produces a detectable difference in measured results at the two selected LED wavelengths. Appropriate dyes include Bromophenol Blue and Crystal Violet. The amount of dye added to the control solution may be varied, in order to account for various factors understood by one having skill in the art, such as reagent system performance and monitor apparatus design considerations. Further, the spectral shape of a fluid sample may be altered by adding other ingredients which alter measurable optical properties, such as phosphorescing materials instead of dyes.

A representative control solution is formulated as shown in Table 1 in amounts sufficient to make 1000 mL of solution.

TABLE 1

| | |
|---|---|
| Sodium Citrate | 58.80 g |
| Glycerol | 40.00 g |
| Sodium Hydroxide | As Needed |
| Hydrochloric Acid | As Needed |
| Acid Red Dye #1[1] | 0.50 g |
| Bromophenol Blue Sodium Salt[2] | 3.00 g |
| Glucose | 1.85 g[3] |
| Stabilizers/Preservatives | 48.00 g |
| Deionized Water | Sufficient to total 1000 mL |

[1]Azophloxine [$C_{18}H_{13}N_3Na_2O_8S_2$]
[2]3', 3", 5', 5"-Tetrabromophenolsulfonephthalein sodium salt [$C_{19}H_9Br_4NaO_5S$]
[3]Varies with product target level Distinguishing the type of test being conducted in the meter system in the manner described above can be performed instantaneously in the case of the standard test, because the strip sensor is not tripped while reflectance values are being detected by the optical block of the monitor apparatus. Distinguishing between the analytical test and the control test generally takes place after a suitable incubation period has transpired between the sample fluid and the reagent system, such that reaction products can be formed and optically detected.

A decision table appears below as Table 2, summarizing the principles of operation of the illustrative embodiment described hereinabove:

TABLE 2

| Test Type | % R @ 610 nm ≈ % R @ 660 nm? | Strip Sensor Tripped? |
|---|---|---|
| Analytical (blood) | Yes | Yes |
| Control | No | Yes |
| Standard | Yes or No | No |

In accordance with the invention, the above described spectral analysis can be applied to any type of test strip that has a distinct spectral shape for a given sample type. Of course, LED wavelengths may be selected from other than 660 nm and 610 nm, depending on the reagent system, to allow the meter to both accurately measure the level of analyte in the sample applied to the test strip, and provide distinguishable spectral curves between an analytical element and a control element, or even between different analytical elements. If different analytical elements were to be distinguished one from another, the reagent system of one type can contain dye particles embedded in the strip as is known in the art. In this way, tests between, for example, glucose and cholesterol might be distinguished using the principles described hereinabove. Also, additional LEDs can be integrated into the optical block, providing an additional data channel upon which a decision can be based.

Also, as shown above in table 1, the standard test is the only test which does not trip the strip sensor, therefore there is no need to ascertain whether the values returned on the 610 nm and 660 nm data channels are substantially equal. For example, if the standard test used a test element where the % R returned at 610 nm and 660 nm were substantially equal, another test type can be provided that would rely on a difference between 610 nm and 660 nm. As an example, a cholesterol test strip can have a notch in its leading edge so as to not trigger the strip sensor, and have a reagent system such that, at a decision point, there is a measurable relative difference between 610 nm and 660 nm. The standard test can be further identified by the absolute returns on the 610 nm and 660 nm channel, for example by providing reflectance values outside the range returned by analytical or control elements. Once the test type is identified as the standard test, which can be instantaneous due to the involvement of the strip sensor, the meter might display % R values instead of analytical values, and the verification by the user can be to compare the % R provided with the standard strip with the % R displayed by the device.

As described above, meter system 10 includes a memory for storing at least successive final glucose values. The memory may hold a collection of successive final glucose values, such as, for example, 365 values. With the capacity of modern subminiature memory chips, a very large amount of data can be reliably stored. These final values can be recalled by pressing a control button 16. Further, meter system 10 may include a data port or a modem assembly for downloading the stored final glucose values to another computer system. The computer system receiving the downloaded final glucose values could be a home PC, or that of a doctor, or a website operator, or any other person or organization for providing assistance to the user in monitoring their glucose levels, or for collecting data on diabetes management on a community regional national or international basis. The modem assembly can be of any configuration (e.g. TCP/IP or ATM), or those having wireless communication capabilities (e.g. those using GSM, WAP, CDMA, etc.). One such modem is described in copending commonly-assigned U.S. patent application Ser. No. 09/512,919, filed Feb. 25, 2000, the contents of which are hereby incorporated by reference.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for automatically selecting test types in an analytical meter system, comprising:
   providing a test element, said test element belonging to one of a plurality of test element types, said test element including a reaction site, said reaction site having an optically detectable condition formed by a reaction between a reagent and an analyte of a sample;
   inserting said test element into an analytical meter system;
   measuring a first optical property of the test element at said reaction site;
   measuring a second optical property of the test element at said reaction site;
   distinguishing said test element by identifying a predetermined relationship between said first and second optical properties; and
   selecting a test type based at least in part upon the results of said distinguishing step.

2. The method of claim 1, wherein said plurality of test element types include analytical elements.

3. The method of claim 1, wherein said plurality of test element types include control elements.

4. The method of claim 1, wherein said plurality of test element types include standard elements.

5. The method of claim 1, wherein said first and second optical properties are absorbance at predetermined wavelengths.

6. The method of claim 5, wherein each of said absorbances are measured by taking at least one reflectance measurement.

7. The method of claim 6, wherein said predetermined relationship comprises a relative difference in percent reflectance which is substantially constant over a range of measured percent reflectance values.

8. The method of claim 1, wherein said sample comprises a biological fluid.

9. The method of claim 8, wherein said biological fluid comprises a fluid selected from the set consisting of: whole blood, blood serum, and blood plasma.

10. The method of claim 1, wherein said sample comprises a control solution, said control solution containing a substance for modifying at least one of said first or second optical properties.

11. The method of claim 10, wherein said substance for altering at least one of said first or second optical properties is a dye.

12. The method of claim 11, wherein said dye is selected from the group consisting of: Bromophenol Blue and Crystal Violet.

13. The method of claim 3, wherein said standard element comprises an element having known first and second optical properties.

14. The method of claim 1, wherein the step of inserting said test element further comprises the step of automatically either positively or negatively activating a switch based on the configuration of the test element.

15. The method of claim 14, wherein said selecting step is based at least in part upon the activation state of said switch.

16. The method of claim 1, further comprising the step of performing the test selected in said selecting step.

17. The method of claim 16, further comprising the step of displaying the results of said test performed in said performing step.

18. The method of claim 16 further comprising the step of storing data based at least in part according to the results of said selecting step.

19. The method of claim 18, where said storing step further comprises storing data classified according to test type.

20. A meter system for performing one of a plurality of test types on a test element, where the test element is inserted into the meter system and belongs to one of a plurality of test element types, said meter system comprising:
   a first light emitting diode selectively discharging light at a first wavelength;
   a second light emitting diode selectively discharging light at a second wavelength;
   at least one light detector for measuring light emitted from the first and second light emitting diodes and reflected from a reaction site on a test element, said reaction site having an optically detectable condition formed by a reaction between a reagent and an analyte of a sample; and
   a processor for distinguishing said test element by identifying a predetermined relationship between said first and second optical properties, and further for selecting a test type based at least in part upon the results of said distinguishing.

21. The meter system of claim 20, wherein said test type performed by the meter system comprises a glucose test, and wherein said sample comprises whole blood.

22. The meter system of claim 20, wherein the processor distinguishes at least an analytical element from a control element.

23. The meter system of claim 20, said meter further comprising a memory for separately storing results of each test type.

24. The meter system of claim 20, wherein the light discharged from the first and second light emitting diode has a wavelength within the range of 600 nm to 700 nm.

25. The meter system of claim 24, wherein the wavelength emitted from the first light emitting diode has a wavelength of approximately 660 nm.

26. The meter system of claim 24, wherein the wavelength emitted from the second light emitting diode has a wavelength of approximately 610 nm.

27. A method for distinguishing a control element from an analytical element in a meter system, comprising:

programming said meter with control element reflectance characteristics;

inserting a test element into said meter, said test element being either a control element or an analytical element, said test element including a reaction site, said reaction site having an optically detectable condition formed by a reaction between a reagent and an analyte of a sample;

measuring at two predetermined wavelengths a set of reflectance values reflected from said reaction site on said test element; and distinguishing whether said test element is a control element or an analytical element based on the conformity of said reflectance values obtained by said measuring step with said control element reflectance characteristics programmed in said meter.

* * * * *